(12) United States Patent
Tranchand-Bunel

(10) Patent No.: US 7,803,378 B2
(45) Date of Patent: Sep. 28, 2010

(54) ANTIGEN IMITATING EXTRACELLULAR AREAS OF MEMBRANE PROTEINS OF TYPE III PRODUCED FROM INTRACELLULAR PATHOGENIC MICRO-ORGANISMS, DERIVED CONFORMATIONAL ANTIBODIES AND THE USE THEREOF

(75) Inventor: Denis Tranchand-Bunel, Ronchin (FR)

(73) Assignees: Centre National de la Recherche Scientifique, Paris FRX; Universite de Rouen, Mont Saint Aignan Cedex (FR); Universite de Lille 2, Lille (FR)

( * ) Notice: Subject to any disclaimer, the term of this patent is extended or adjusted under 35 U.S.C. 154(b) by 895 days.

(21) Appl. No.: 10/544,081

(22) PCT Filed: Jan. 28, 2004

(86) PCT No.: PCT/FR2004/000190

§ 371 (c)(1),
(2), (4) Date: Aug. 9, 2006

(87) PCT Pub. No.: WO2004/069140

PCT Pub. Date: Aug. 19, 2004

(65) Prior Publication Data

US 2008/0075717 A1  Mar. 27, 2008

(30) Foreign Application Priority Data

Jan. 28, 2003  (FR) .................................. 03/00943

(51) Int. Cl.
*A61K 39/00* (2006.01)
*C07K 5/00* (2006.01)
(52) U.S. Cl. .................................... 424/184.1; 530/300
(58) Field of Classification Search .................. None
See application file for complete search history.

(56) References Cited

U.S. PATENT DOCUMENTS 6,723,695 B1 * 4/2004 Burrows et al. ................. 514/2
7,091,324 B2 * 8/2006 Foung et al. .............. 530/388.3

FOREIGN PATENT DOCUMENTS

| EP | 1229043 A1 * | 7/2002 |
| EP | 1 229 043 A | 8/2002 |
| EP | 1 229 043 A1 * | 8/2002 |
| JP | 2002-255997 | 9/2002 |
| WO | WO 90/04176 | 4/1990 |
| WO | WO 01/37868 A1 | 5/2001 |
| WO | WO 02/060930 A2 * | 8/2002 |
| WO | WO 03/048337 * | 6/2003 |

OTHER PUBLICATIONS

Glenn et al. Journal of Virology, 1999, vol. 73, p. 6953-6963.*
Su et al. Journal of Experimental Medicine, 1990, vol. 172, p. 203-212.*
Olsen et al Journal of Virology, 1999, vol. 73, p. 8975-8981.*
Greer et al. Journal of Immunology, 2001, vol. 166, p. 6907-6913.*
Database Swiss Prot 386 aa, latent Membrane Protein 1 (LMP-1), Jul. 21, 1986, p. 63.
Tsukamoto K et al., "Involvement of Epstein-Barr virus latent membrane protein 1 in disease progression in patients with idiopathic pulmonary fibrosis", Nov. 2000, *Thorax*, vol. 55, NR 11, pp. 958-961.
Xu, et al., "Analysis and significance of anti-latent membrane protein-1 antibodies in the sera of patients with EBV-associated diseases", *Jouranl of Immunology*, vol. 164, No. 5, 2000, pp. 2815-2822.
Delbende et al, "Induction of Therapeutic Antibodies by Vaccination against External Loops of Tumor-Associated Viral Latent Membrane Protein," *Journal of Virology*, 2009, vol. 83(22), pp. 11734-11745.
Freuhling et al, "Identification of Latent Membrane Protein 2A (LMP2A) Domains Essential for the LMP2A Dominant-Negative Effect on B-Lymphocyte Surface Immunoglobulin Signal Transduction," *Journal of Virology*, 1996, vol. 70(9), pp. 6216-6226.
Middleton et al., "Plasma Membrane-Associated LMP1 Detected by Antibodies to the Putative LMP1 Extracellular Domains," Meeting Program for Tenth International Symposium on EBV and Associated Diseases, Cairns, Australia, Jul. 16-21, 2002, International Association for Research on Epstein-Barr virus and Associated Diseases, Poster 66.
Middleton et al., "Human Monoclonal Antibodies Reactive With LMP1 Extracellular Domains," Meeting Program for Tenth International Symposium on EBV and Associated Diseases, Cairns, Australia, Jul. 16-21, 2002, International Association for Research on Epstein-Barr virus and Associated Diseases, Poster 67.
Rowe et al., "Monoclonal Antibodies to the Latent Membrane Protein Of Epstein-Barr Virus Reveal Heterogeneity of the Protein and Inducible Expression in Virus-transformed Cells," *J gen. Virol.*, 1987, vol. 68, pp. 1575-1586.

* cited by examiner

*Primary Examiner*—Zachariah Lucas
*Assistant Examiner*—Agnieszka Boesen
(74) *Attorney, Agent, or Firm*—Alston & Bird LLP

(57) ABSTRACT

An antigen derived from an intracellular pathogenic microorganism characterized in that it comprises at least on peptidic fragment which essentially consists of the concatenation of sequences of at least two extracellular adjacent areas in the native structure of a membrane protein of type III of said intracellular pathogenic micro-organism, derived conformational antibodies and the application hereof.

2 Claims, 17 Drawing Sheets

| Latency | Viral Ag present | Cellular genes | Associated Pathologies |
|---|---|---|---|
| Type I | EBNA1<br>BARF0 | HLA class 1<sup>-</sup><br>TAP-1<sup>-</sup> and TAP-2<sup>-</sup><br><br>*CD8 cytolysis resistant?* | Burkitt's lymphoma |
| Type II | EBNA1<br>LMP1 and LMP2<br>BARF0 | HLA class 1<sup>+</sup><br>TAP-1<sup>+</sup> and TAP-2<sup>+</sup><br><br>*CD8 cytolysis sensitive?* | Hodgkin's disease<br>Nasopharyngeal carcinoma<br>Gastric carcinoma<br>Nasal T/NK lymphoma<br>Breast cancer? |
| Type III | EBNA1-6<br>LMP1 and LMP2<br>BARF0 | HLA class 1<sup>+</sup><br>TAP-1<sup>+</sup> and TAP-2<sup>+</sup><br><br>*CD8 cytolysis sensitive?* | Post-transplantation lymphoproliferative disease<br>AIDS-related lymphomas |
| Type IV ? | EBNA1 (+/-)<br>LMP2 | HLA class 1<sup>+</sup><br>TAP-1<sup>+</sup> and TAP-2<sup>+</sup><br><br>*CD8 cytolysis sensitive?* | Healthy carriers |

Figure 1

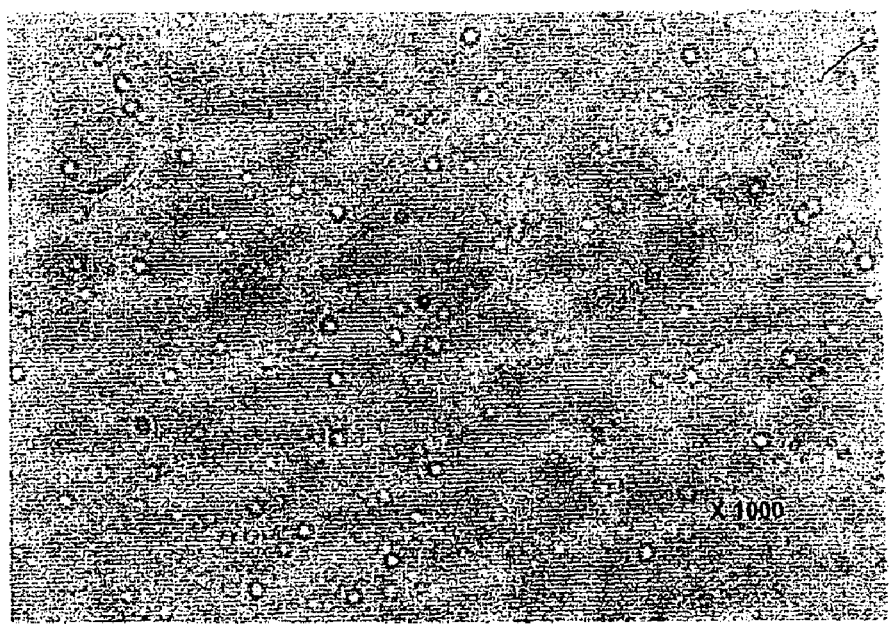
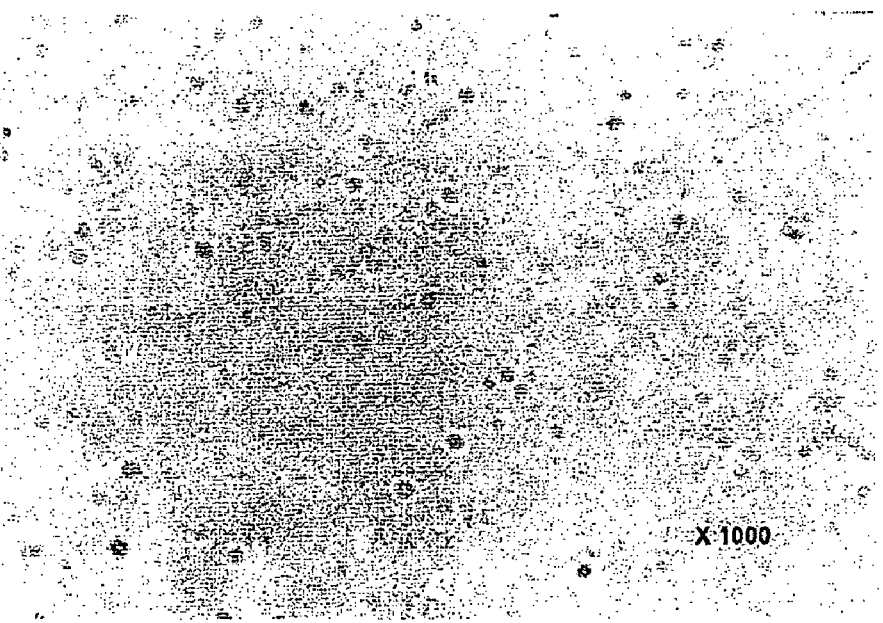
Figure 4

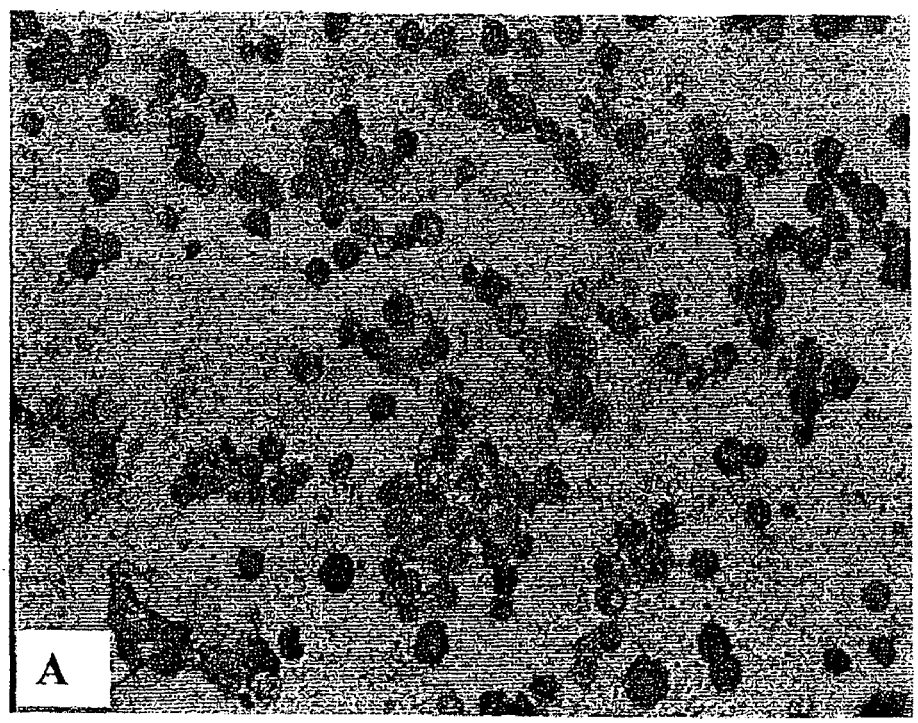
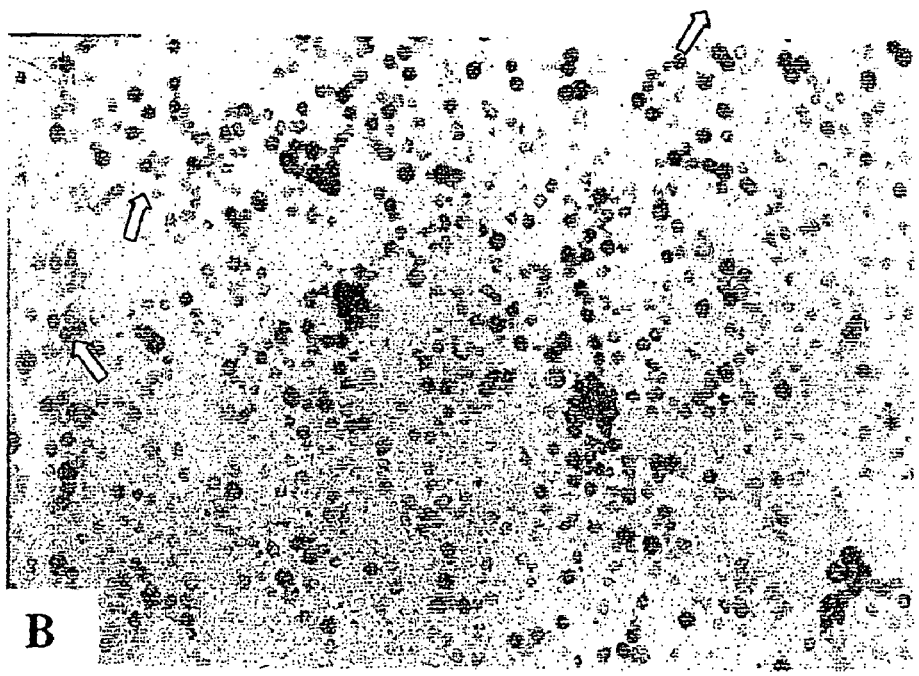
Figure 8

A  Healthy carrier No. 1
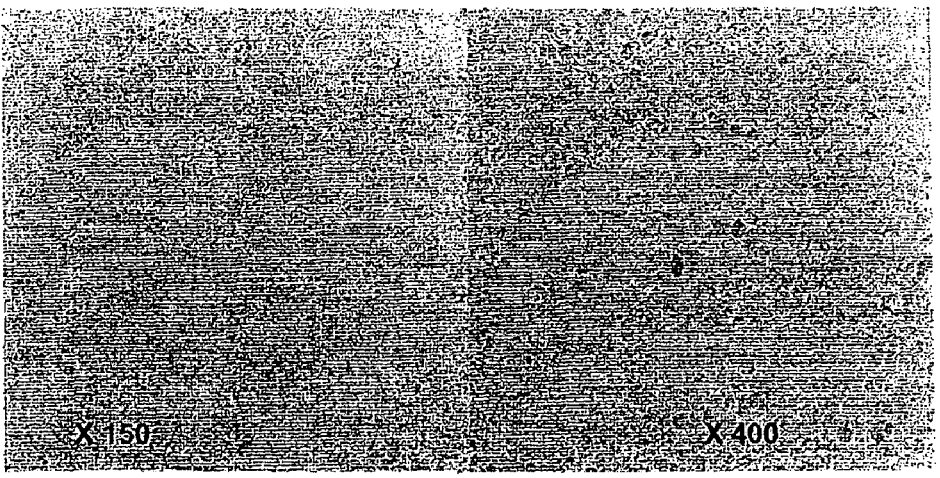
B  Healthy carrier No. 2
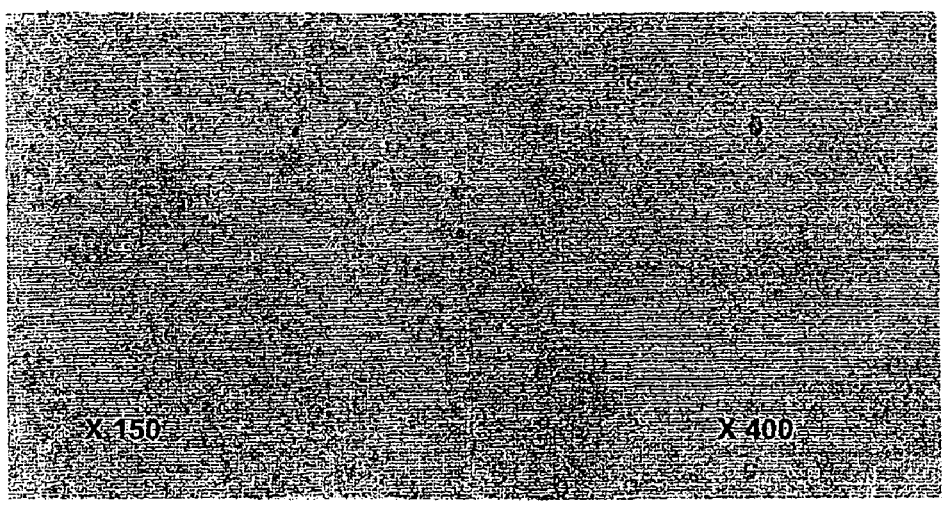
C  Healthy carrier No. 3
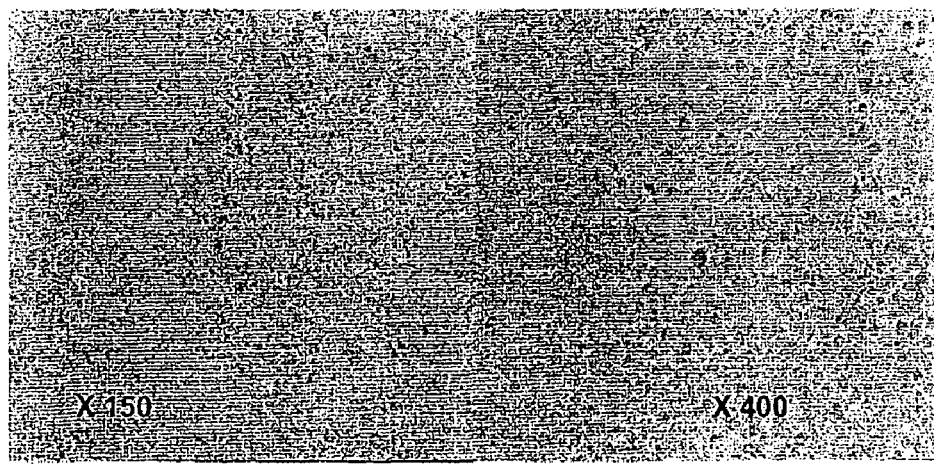
Figure 9

| Cell cycle | A, C and E* | B and D* | F* |
|---|---|---|---|
| G0/G1 | 49.5 % | 49.4 % | 38.7 % |
| S | 11.4 % | 12.6 % | 5.7 % |
| G2/M | 14.5 % | 16.9 % | 4.7 % |
| Apoptosis | 16.4 % | 13.3 % | 48.9 % |

* Interassay variation < 10%

Figure 11

ANTIGEN IMITATING EXTRACELLULAR AREAS OF MEMBRANE PROTEINS OF TYPE III PRODUCED FROM INTRACELLULAR PATHOGENIC MICRO-ORGANISMS, DERIVED CONFORMATIONAL ANTIBODIES AND THE USE THEREOF

FIELD AND BACKGROUND OF THE INVENTION

The present invention relates to antigens that mimic the structure of extracellular domains of type III membrane proteins derived from intracellular pathogenic microorganisms, to the conformational antibodies prepared from said antigens, and to the uses thereof for detecting, preventing and treating latent or chronic infections with these microorganisms, and associated pathologies, in particular tumor or autoimmune pathologies.

Certain intracellular microorganisms (viruses, bacteria, fungi, parasites) responsible for latent or chronic infections pose public health problems in many countries; by way of nonlimiting example, mention may be made of viruses such as the hepatitis C virus (HCV), the human immunodeficiency virus (HIV), viruses of the herpesviridae family [Epstein-Barr virus (EBV); cytomegalo virus (CMV); Kaposi's sarcoma herpesvirus (KSHV); herpes simplex virus (HSV); varicella-zoster virus (VZV)] and the hepatitis B virus (HBV), and also intracellular bacteria, in particular Chlamydia trachomatis and *Mycobacterium* tuberculosis.

These intracellular microorganisms are characterized by their ability to persist in the latent state throughout the life of the host (human or animal) without being eradicated by the immune system in subsequence to the primary infection; this host-virus relationship, which is very complex and poorly elucidated, involves viral or bacterial mechanisms that avoid the immune response, such as genetic variability (HCV, HIV) and the expression of proteins that modulate the immune response [EBNA1 protein (EBV)].

Although infection with these intracellular microorganisms is clinically silent in most individuals, some of them, in particular immunodepressed individuals, develop chronic pathologies, in particular pulmonary (*Mycobacterium* tuberculosis), genital and ocular (Chlamydia trachomatis) pathologies, tumor pathologies (EBV, HCV, HBV, KSHV) or autoimmune pathologies (EBV). For example, EBV is associated with a large number of tumor pathologies: Burkitt's lymphoma (Central Africa), nasopharyngeal carcinoma (South East Asia), gastric carcinoma, Hodgkin's disease, nasal lymphomas and breast cancer, post-transplantation lymphoproliferative diseases, and AIDS-related lymphomas, and also autoimmune pathologies: rheumatoid arthritis, disseminated lupus erythematosus and Sjögen's syndrome.

The antigens expressed during the chronic phase or latency phase represent target antigens for immunization for preventive or therapeutic purposes, and for the diagnosis of infections with these intracellular microorganisms and of associated pathologies.

For example, latent EBV infection results in the expression of a limited number of viral genes encoding, respectively, for six nucleus proteins (EBNA-1, -2, -3a, -3b and -3c, and LP) and two membrane proteins [LMP1 and LMP2 (LMP2A/LMP2B)]; at least three types of latency (I, II, III) representing at least three distinct expression profiles are associated with distinct tumor pathologies, and a fourth type of latency (IV) representing an expression profile different from the above, could be associated with an asymptomatic state (healthy carriers) (FIG. 1).

It is generally accepted that latent EBV infection is essentially controlled by cellular immunity mediated by a population of CD8+ cytotoxic T lymphocytes (CTLs), specific for EBV latency proteins, essentially for the EBNA proteins, whereas the humoral immunity directed against the EBV latency proteins does not play a protective role in infected individuals. The loss of this control, due either to the decrease in activity of the effectors (CTLs) or to the decrease in target recognition (decrease in class I antigen presentation), would severely compromise the host's ability to control the proliferation of the EBV-infected cells and would be responsible for the development of malignant tumors related to latent EBV infections.

Thus, immunotherapy against EBV-related malignant tumors essentially makes use of the in vitro activation of autologous CTLs, from patients, against latency proteins and of reimplantation thereof, with more or less effectiveness (for a review, see Khanna R. et al., TRENDS in *Molecular Medicine*, 2001, 7: 270-276). This cell therapy has the drawback of being very expensive and laborious to implement.

Latency antigen detection, which is useful for diagnosing latent EBV infections and associated pathologies, requires a cell permeabilization step before said cells are brought into contact with the antibodies, which is tricky to carry out.

To more effectively combat latent or chronic infections with these intracellular pathogenic microorganisms, and the associated pathologies, there exists a real need for novel antigens for preventive and therapeutic immunization, and also diagnosis.

Among the antigens expressed during the chronic phase or latency phase of the infection, mention may be made of type III membrane proteins, characterized by transmembrane domains that separate short extracellular domains (EDs) and intracellular domains (IDs) and are bordered by larger N- and/or C-terminal intracellular domains; FIG. 2 illustrates the hypothetical structure of type III membrane proteins having 2n membrane domains. By way of nonlimiting example of type III membrane proteins having 2n transmembrane domains, that are expressed during the chronic or latency phase of the infection, mention may be made of the EBV LMP1 and LMP2A proteins (accession number in the Swissprot database, respectively P03230 (SEQ ID NO: 29) and P13285 (SEQ ID NO: 30), with reference to the sequence of the EBV strain B95.8), the KSHV LAMP K15-P and LAMP K15-M proteins (Genbank accession numbers, respectively AAD45297 (SEQ ID NO: 31) and AAD45296 (SEQ ID NO: 32)), the HCV p7, NS2 and NS4B proteins (EMBL accession number AF009606 (SEQ ID NO: 33)), the *Chlamydia trachomatis* MOMP protein (*Major Outer Membrane Protein*; NCBI accession number AF352789 (SEQ ID NO: 34)) and the *Mycobacterium tuberculosis* MmpI 1 to 12 transport proteins.

The absence of antibodies directed against the type III membrane proteins, in individuals suffering latent or chronic infection with these microorganisms, indicates that these proteins are not accessible at the surface of the infected cells or that extracellular domains are not immunogenic (FIG. 2).

The absence of antibodies directed against the extracellular domains, observed when laboratory animals are immunized with recombinant LMP1 and LMP2 proteins, indicates rather that their extracellular domains are not immunogenic (Hennessy et al., K., *Proc. Natl. Acad. Sci. USA,* 1984, 81: 7207-7211) and with LMP2 (Longnecker et al., *J. Virol.,* 1990., 64: 3219-3226). In fact, all the anti-LMP1 antibodies described recognize more or less well-identified fragments of the intracellular regions of the LMP1 or LMP2A proteins, namely, for LMP1: CS1-4 (pool of 4 monoclonal antibodies, Dako, Glostrup, Denmark), S12 (Dr Elliott Kieff, Harvard Medical School, Boston, Mass.), OT22C and OT22CN (Organon Teknika, Boxtel, The Netherlands). Antibodies directed against extracellular domains of the LMP1 and LMP2 proteins have nevertheless been obtained by immunizing rabbits with synthetic peptides representing the sequence of a single extracellular domain coupled to a carrier protein (European application EP 1229043). However, the antibodies obtained are non-conformational antibodies which do not recognize the natural antigen expressed at the surface of the cells affected by latent EBV infection, but only the denatured antigen or a fragment thereof (linear peptide representing a single extracellular domain). In addition, these antibodies do not exhibit any significant biological activity (complement-dependent cytotoxic activity or ADCC for antibody dependent cellular cytotoxicity).

No antibodies or antigens currently therefore exist that are effective for the treatment (serotherapy or preventive or therapeutic immunization) of latent or chronic infections with the intracellular pathogenic microorganisms as defined above, and of the associated pathologies, in particular EBV infection and the associated tumor pathologies.

SUMMARY OF THE INVENTION

Consequently, the inventor gave itself the aim of providing antigens and antibodies that are more successful at meeting practical needs. Surprisingly, the inventor has found that chimeric antigens that mimic the structure of the extracellular domains of the type III membrane proteins of the intracellular pathogenic microorganisms as defined above induce the production, in immunized individuals, of conformational antibodies that specifically recognize said type III membrane proteins in the native form, and that have both complement-dependent cytotoxic activity and pro-apoptotic activity, with respect to cells expressing said type III membrane proteins at their surface.

Among these antigens, the chimeric antigens that mimic the structure of the extracellular domains of EBV latency membrane proteins induce the production, in immunized individuals, of conformational antibodies that specifically recognize the LMP1 and LMP2A proteins in the native form. The inventor has also shown that these conformational antibodies have complement-dependent cytotoxic activity and pro-apoptotic activity, with respect to cells expressing said LMP1 and LMP2 proteins at their surface, and are capable of preventing the appearance and the development, in mice, of tumors expressing said LMP1 and LMP2 proteins at their surface; this activity was demonstrated in serotherapy experiments (antibody injection) and preventive immunization experiments (antigen injection).

Such conformational antibodies are useful for detecting, using a suitable biological sample (whole blood, peripheral blood mononuclear cells, tumor biopsy), patients suffering from latent or chronic infections or from pathologies induced by the intracellular pathogenic microorganisms as defined above, in particular by EBV; these antibodies that recognize the type III membrane proteins in the native form, in a sensitive and specific manner, do not in any way require prior steps consisting of denaturation and/or permeabilization of the cells and, optionally, of purification of the infected cells (cell enrichment step), before the step in which the antibody is brought into contact with the biological sample to be tested.

In addition, such conformational antibodies are capable of specifically lysing the cells, infected with intracellular pathogenic microorganisms, which express the type III membrane proteins at their surface; these antibodies are useful in serotherapy, for:

eradicating latent or chronic infections with the intracellular pathogenic microorganisms as defined above, in particular EBV, and preventing the associated pathologies by destroying the reservoir of viral latency consisting of the infected cells expressing the type III membrane proteins (B lymphocytes expressing LMP1 and/or LMP2A in the case of EBV, hepatocytes expressing p7, NS2 and NS4B in the case of HCV, and lymphoid cells expressing LAMP K15-P and LAMP K15-M in the case of KSHV), treating malignant tumors associated with latent or chronic infections with intracellular pathogenic microorganisms as defined above, in particular EBV, KSHV and HCV, by targeting and destroying the cancerous cells expressing the type III membrane proteins as defined above (LMP1 and/or LMP2A (EBV), p7 HCV), LAMP K15-P and/or LAMP K15-M (KSHV)).

Similarly, the antigens that mimic the structure of the extracellular domains of the type III latency membrane proteins of the intracellular pathogenic microorganisms as defined above, which are capable of inducing the production, in immunized individuals, of such conformational antibodies having cytotoxic activity, are also useful as a vaccine composition for preventing or treating latent infections with these intracellular microorganisms, and the associated pathologies, in particular EBV infection and the associated malignant tumors.

Consequently, a subject of the present invention is an antigen derived from an intracellular pathogenic microorganism, characterized in that it comprises at least one peptide fragment consisting essentially of the concatenation of the sequences of at least two adjacent extracellular domains in the native structure of a type III membrane protein of said intracellular pathogenic microorganism.

For the purpose of the present invention, the term "type III membrane protein" is intended to mean a membrane protein characterized by transmembrane domains that separate short extracellular domains (EDs) and intracellular domains (IDs) and are bordered by larger N- and/or C-terminal intracellular domains (FIG. 2), as defined above, in particular a membrane protein having 2n transmembrane domains, as defined above.

The invention encompasses the antigens derived from the type III membrane proteins of any intracellular pathogenic microorganism as defined above, and from the derived variants.

In accordance with the invention, the extracellular domains of the type III membrane proteins are as defined in the structural model of the native LMP1 protein shown in FIG. 3, which applies by analogy to the other type III membrane proteins. Thus, the adjacent extracellular domains of these proteins correspond to those which are close in the native structure of the protein, the first domain corresponding to that located at the N-terminal end of the protein.

The sequences of the various extracellular domains of the type III membrane proteins correspond to those located between two successive transmembrane domains (numbered TM1 to TMn, from the N-terminal end to the C terminal end of the proteins), the first transmembrane domain corresponding to an odd number. These sequences are deduced from the sequence of the various transmembrane domains of the type III membrane proteins, which is determined by analysis of the hydrophobicity of the amino acid sequence of said proteins, using an appropriate program, in particular:

TM-Finder, and
TMHMM.

For example, the LMP1 protein of the EBV strain B95-8 (accession number P03230 (SEQ ID NO: 29) in the Swissprot database) has 6 potential transmembrane domains ($TM_1$ to $TM_6$) corresponding, according to the program used, to positions 25 to approximately 42-44, approximately 49-52 to 72, 77 to approximately 97-98, 105 to 125, 139 to 159 and approximately 164-166 to 186. The sequences located between the domains $TM_1$ and $TM_2$, $TM_3$ and $TM_4$, $TM_5$ and $TM_6$ correspond to those of the three extracellular domains (ED1 to ED3), the first domain of the protein corresponding to that located at the N-terminal end of LMP1:

```
LMP1-ED1    (positions 45 to 51, SEQ ID No. 1)
SDWTGGA
or

VMSDWT      (positions 43 to 48, SEQ ID No. 24)

LMP1-ED2    (positions 98 to 104, SEQ ID No. 2)
WNLHGQA
or

NLHGQA.     (positions 99 to 104, SEQ ID No. 25)

LMP1-ED3    (positions 160 to 163, SEQ ID No. 26)
LQQN
or

LQQNWW.     (positions 160 to 165, SEQ ID No. 3)
```

Similarly, for the LMP2A protein of the EBV strain B95-8 (accession number P13285 (SEQ ID NO: 30) in the Swissprot database), the sequence of the 6 extracellular domains (ED1 to ED6) is deduced from that of the 12 potential transmembrane domains:

```
LMP2-ED1              (positions 142 to 149,
SCFTASVS              SEQ ID No. 4)

LMP2-ED2              (positions 199 to 207,
RIEDPPFNS             SEQ ID No. 5)

LMP2-ED3              (positions 260 to 266,
DAVLQLS               SEQ ID No. 6)

LMP2-ED4              (positions 317 to 320,
GTLN                  SEQ ID No. 7)

LMP2-ED5              (positions 374 to 391,
SILQTNFKSLSSTEFIPN    SEQ ID No. 8)

LMP2-ED6              (positions 444 to 449,
SNTLLS.               SEQ ID No. 9)
```

According to an advantageous embodiment of the invention, said peptide fragment comprises at least one heterologous linking sequence of 1 to 5 amino acids that are identical to or different from one another, preferably of 1 to 3 amino acids, preceding the sequence of one of the extracellular domains as defined above.

According to an advantageous arrangement of this embodiment, said amino acids are different from those present in the sequences of said extracellular domains.

According to another advantageous arrangement of this embodiment, all the sequences of the adjacent extracellular domains, with the exception of those located at the N- and/or C-terminal ends of said peptide fragment, are preceded by a heterologous linking sequence as defined above.

According to yet another advantageous arrangement of this embodiment, all the sequences of the adjacent extracellular domains of said peptide fragment are preceded by a heterologous linking sequence as defined above:

In accordance with the invention, the amino acid residues of the linking sequence have a side chain comprising a reactive function. Among these amino acids, mention may be made of polar amino acids comprising a function: —OH [serine (S), threonine (T) or tyrosine (Y)], —SH [cysteine (C)], —$NH_2$ [lysine (K) or arginine (R)], —COOH [aspartic acid (D) or gluatmic acid (E)], and polar amino acids comprising a side chain functionalized by the addition of a reactive function, in particular a chloro- or bromoacetyl that is reactive with thiol groups or a hydrazine group that is reactive with aldehydes.

According to another advantageous arrangement of this embodiment, said amino acids are chosen from cysteine (C) and/or lysine (K).

According to yet another advantageous embodiment of the invention, said peptide fragment also includes, between the heterologous linking sequences and the sequences of the extracellular domains and on either side of said sequences of the extracellular domains, a sequence of at least one amino acid, preferably of 1 to 7 amino acids, preferably 2 amino acids, corresponding to that of the transmembrane domain flanking said extracellular domain in the structure of said type III membrane protein.

According to yet another advantageous embodiment of the invention, said antigen is derived from a type III membrane protein selected from the group consisting of: the EBV LMP1 and LMP2A proteins (accession number in the Swissprot database, respectively P03230 (SEQ ID NO: 29)and P13285 (SEQ ID NO: 30), with reference to the sequence of the EBV strain B95.8), the KSHV LAMP K15-P and LAMP K15-M proteins (Genbank accession numbers, respectively AAD45297 (SEQ ID NO: 31) and AAD45296 (SEQ ID NO: 32)), the HCV p7, NS2 and NS4B proteins (EMBL accession number AF009606 (SEQ ID NO: 33)), the *Chlamydia trachomatis* MOMP protein (Major Outer Membrane Protein: NCBI accession number AF352789 (SEQ ID NO: 34)) and the *Mycobacterium tuberculosis* Mmp1 to 12 transport proteins.

According to yet another advantageous embodiment of the invention, said peptide fragment essentially consists of the concatenation of the sequences of 2 to 6 adjacent extracellular domains, preferably 2 to 3 adjacent extracellular domains, in the native structure of said protein.

According to an advantageous arrangement of one of the above embodiments, said antigen is derived from the EBV LMP1 or LMP2A proteins and is selected from the sequences SEQ ID numbers 10, 11 and 13 to 23.

According to yet another advantageous embodiment of the invention, said antigen comprises at least two peptide fragments as defined above, derived from different type III membrane proteins; preferably, said fragments are combined covalently by means of their C-terminal or N-terminal ends (peptide bond) or else by means of a reactive function on the side chain of an amino acid in their linking sequence.

The invention also encompasses the antigens consisting of the sequences that are functionally equivalent to the sequences as defined above, i.e. capable of inducing the production, in immunized individuals, of conformational antibodies that specifically recognize the type III membrane proteins in the native form, and that have complement-dependent cytotoxic activity and pro-apoptotic activity, with respect to cells expressing said type III membrane proteins at their surface. Among these sequences, mention may, for example, be made of the sequences derived from the above sequences by:

substitution and/or deletion and/or addition of one or more amino acids of the sequences as defined above, modification of at least one peptide bond —CO—NH— of the peptide chain of the antigen as defined above, in particular by replacement with a bond different from the bond —CO—NH— (methyleneamino, carba, ketomethylene, thioamide, etc.) or by the introduction of a bond of retro or retro-inverso type, and/or substitution of at least one amino acid of the peptide chain of the antigen as defined above, with a non-proteinogenic amino acid residue.

The term "non-proteinogenic amino acid residue" is intended to mean any amino acid that does not form part of the makeup of a natural protein or peptide, in particular any amino acid in which the carbon bearing the side chain R, i.e. the group —CHR—, located between —CO— and —NH— in the natural peptide chain, is replaced with a unit that is not part of the makeup of a natural protein or peptide.

According to an advantageous embodiment of the invention, at least one of the amino acids of said heterologous linking sequence is covalently attached to at least one carrier protein or at least one lipid.

According to an advantageous arrangement of this embodiment, at least two amino acids, each derived from the unique linking sequence of different peptide fragments (of identical or different sequence) are attached to a carrier protein; the antigen thus obtained comprises at least two identical or different peptide fragments covalently attached to a single carrier protein (intermolecular coupling, FIG. 3).

According to another advantageous arrangement of this embodiment, at least two amino acids derived from one or more heterologous linking sequence(s) of a single peptide fragment are each attached to a lipid; the antigen thus obtained comprises a single peptide fragment covalently attached to several lipid molecules (intramolecular coupling, FIG. 3). Such lipopeptide antigens are capable of self-assembling into lipid bilayers or vesicles that mimic the surface of a cell infected with an intracellular pathogenic microorganism expressing a type III membrane protein as defined above.

Such a combination advantageously makes it possible to increase the immunogenicity of the antigen according to the invention.

The lipids may be coupled to the peptide antigen by means of one or more α-amino functions or by means of one or more reactive functions of the side chain of an amino acid of the peptide portion; they may comprise one or more saturated or unsaturated, linear or branched $C_{4-20}$ fatty acid-derived chains (palmitic acid, oleic acid, linoleic acid, linolenic acid, 2-amino hexadecanoic acid, pimelautide, trimexautide) or one or more steroic groups (cholesterol and derivatives). Advantageously, the lipid(s) is (are) attached: via an amide bond to the α—NH$_2$ or ε—NH$_2$ function of a lysine (Lys N$^\epsilon$ (palmitoyl)) or to any amino function of said junction peptide, via a thioester or thioether bond to a thiol function of cysteine, via an ether bond to an alcohol function of said junction peptide or else via an ester bond to an acid or alcohol function of said junction peptide. Preferably, the lipid(s) is (are) branched via ether, thioether, ester and thioester bonds, which are more immunogenic than the amide bond. Even more preferably, the lipid(s) is (are) branched via a thioester bond, which is both more labile and more immunogenic (Greer et al., *J. Immunol.*, 2001, 166: 6907-6913). Among the preferred lipid groups, mention may in particular be made of: Asp (cholesteryl), Glu (cholesteryl), Ser (palmitoyl), Cys (palmitoyl), Ser (cholesteryl) or Cys (cholesteryl).

A subject of the present invention is also micelles or vesicles of a lipopeptide antigen as defined above.

The carrier protein can be coupled to the peptide antigen by any appropriate means; these means, which are known to those skilled in the art, include in particular coupling with glutaraldehyde or bis-dinitrobenzidine. Preferably, the coupling is carried out with a heterofunctional agent such as m-maleimidobenzoyl-N-hydroxysuccinimide (SMCC) or sulfo-SMCC, which specifically couples a thiol function of the antigen (cysteine residue) with an amine function (lysine residue) of KLH, and carbodiimide or its water-soluble derivatives such as 1-ethyldimethylaminopropylcarbodiimide hydrochloride, and m-maleimidocaproyl-3-sulfo-N-hydroxysuccinimide. Preferably, m-maleimidocaproyl-3-sulfo-N-hydroxy-succinimide, which is more immunogenic, is used for coupling the antigen.

Among carrier proteins, mention may in particular be made of KLH (Key hole Limpet Haemocyanin), bovine albumin or other albumins such as those from mouse or rabbit. A preferred carrier protein is KLH, which can be coupled to the antigen via a thioether bond at a cysteine residue, or via an amide bond at a lysine residue, of the heterologous linking sequence as defined above.

A subject of the present invention is also an immunogenic composition, characterized in that it comprises an antigen as defined above, optionally in the form of lipopeptide micelles or vesicles, combined with at least one pharmaceutically acceptable vehicle and, optionally, at least one adjuvant.

The adjuvants used are adjuvants conventionally used in vaccine compositions, such as aluminohydroxide and squalene.

According to another advantageous embodiment of said immunogenic composition, said antigen is combined with:

one or more peptides containing CD4+ T epitopes derived from latency proteins of the intracellular pathogenic microorganisms as defined above, in particular of EBV (Leen et al., *J. Virol.*, 2001, 75: 8649-8659; Paludan et al., *J. Immunol.*, 2002, 169: 1593-1603);

one or more peptides containing multiple CD4+ epitopes, such as the tetanus toxin TT peptide (positions 830-846), the influenza hemagglutinin HA peptide (positions 307-319), PADRE (Pan Dr Epitope, Alexandre J. et al., *Immunity*, 1994, 1: 751-761) and the Plasmodium falciparum LSA3 peptide.

A subject of the present invention is also the use of an antigen as defined above, for preparing a vaccine intended for the prevention or treatment of the latent or chronic infections and of the associated pathologies as defined above, in particular EBV infections and the associated tumoral pathologies.

The antigens according to the invention are prepared by conventional solid-phase of liquid-phase synthesis techniques, known in themselves to those skilled in the art. Alternatively, they can be prepared by recombinant DNA techniques, known in themselves to those skilled in the art.

Consequently, a subject of the present invention is also an isolated nucleic acid molecule, characterized in that it comprises a sequence encoding an antigen as defined above.

A subject of the invention is also probes and primers, characterized in that they comprise a sequence of approximately 10 to 30 nucleotides, corresponding to that located at the junction of the sequences encoding a transmembrane domain and of the sequences encoding an extracellular domain adjacent to the above domain, of a type III membrane protein as defined above; these probes and these primers make it possible to specifically detect/amplify said nucleic acid molecules encoding an antigen according to the invention.

The nucleic acid molecules according to the invention are obtained by conventional methods, known in themselves, according to standard protocols such as those described in *Current Protocols in Molecular Biology* (Frederick M. Ausubel, 2000, Wiley and Son Inc., Library of Congress, USA).

The sequences encoding an antigen according to the invention can be obtained by amplification of a nucleic acid sequence by PCR or RT-PCR or else by screening genomic DNA libraries by hybridization with an homologous probe. For example, they are amplified by PCR using an appropriate pair of primers as defined above.

A subject of the present invention is also a eukaryotic or prokaryotic recombinant vector, characterized in that it comprises an insert consisting of a nucleic acid molecule encoding an antigen as defined above. Many vectors into which it is possible to insert a nucleic acid molecule of interest, in order to introduce it into and to maintain it in a eukaryotic or prokaryotic host cell, are known in themselves; the choice of an appropriate vector depends on the use envisioned for this vector (for example, replication of the sequence of interest, expression of this sequence, maintenance of the sequence in extrachromosomal form or else integration into the host's chromosomal material), and also on the nature of the host cell. For example, viral vectors or nonviral vectors, such as plasmids, can be used.

Preferably, said recombinant vector is an expression vector in which said nucleic acid molecule or one of its fragments is placed under the control of appropriate transcriptional and translational regulatory elements. In addition, said vector can comprise sequences (tags) fused in phase in the 5'-and/or 3'-end of said insert, that are useful for immobilizing, and/or detecting and/or purifying, the protein expressed from said vector. Alternatively, said nucleic acid molecule of interest can be inserted into the sequence encoding a viral capsid protein, at a site that allows exposure of the antigen according to the invention, at the surface of the viral capsid.

These vectors are constructed and introduced into host cells by conventional recombinant DNA and genetic engineerings methods, which are known in themselves.

The subject of the present invention is also eukaryotic or prokaryotic cells modified with a recombinant vector as defined above.

The recombinant vectors and the transformed cells, as defined above, are useful in particular for producing the antigen as defined above.

A subject of the present invention is also an antibody directed against the type III membrane proteins as defined above, characterized in that it is produced by immunization of an appropriate animal with an antigen or an immunogenic composition as defined above.

The invention encompasses the polyclonal antibodies, the monoclonal antibodies, the chimeric antibodies, such as humanized antibodies, and fragments thereof (Fab, Fv, scFv).

For the purpose of the present invention, the term "chimeric antibody" is intended to mean, in relation to an antibody of a particular animal species or of a particular antibody class, an antibody comprising all or part of a light chain and/or of a heavy chain of an antibody of another animal species or of another antibody class.

For the purpose of the present invention, the term "humanized antibody" is intended to mean a human immunoglobulin in which the residues of the CDRs (complementarity-determining regions) that form the antigen-binding site are replaced with those of a nonhuman monoclonal antibody having the desired specificity, affinity or activity. By comparison with nonhuman antibodies, humanized antibodies are less immunogenic and have a prolonged half-life in humans since they have only a small proportion of nonhuman sequences, given that virtually all the residues of the FR (framework) regions and of the constant region (Fc) of these antibodies are those of a human immunoglobulin consensus sequence.

Preferred antibodies are monoclonal antibodies and humanized antibodies.

The antibodies according to the invention, and the fragments thereof, are prepared by conventional techniques known to those skilled in the art, such as those described in Antibodies: A Laboratory Manual, E. Howell and D. Lane, Cold Spring Harbor Laboratory, 1988.

More specifically:

the polyclonal antibodies are prepared by immunization of an appropriate animal with an antigen as defined above, optionally coupled to KLH or to albumin and/or combined with an appropriate adjuvant such as (complete or incomplete) Fruend's adjuvant or alumina hydroxide; after a satisfactory antibody titer has been obtained, the antibodies are harvested by taking the serum of the immunized animals, and are IgG-enriched by precipitation, according to conventional techniques, and then the IgGs specific for the type III membrane proteins are optionally purified by affinity chromatography on an appropriate column to which said protein or the antigen as defined above is attached, so as to obtain a preparation of monospecific IgGs;

the monoclonal antibodies are produced by hybridomas obtained by fusion of B lymphocytes from an animal immunized with the antigen as defined above, with myelomas, according to the Kohler and Milstein technique (Nature, 1975, 256, 495-497); the hybridomes are cultured in vitro, in particular in fermenters, or are produced in vivo, in the form of ascites; alternatively, said monoclonal antibodies are produced by genetic engineering as described in American patent U.S. Pat. No. 4,816,567;

the humanized antibodies are produced by general methods such as those described in international application WO 98/45332;

the antibody fragments are produced from the $V_H$ and $V_L$ regions that have been cloned, from the mRNA of hybridomas or of lymphocytes from the spleen of an immunized mouse; for example, the Fv, scFv or Fab fragments are expressed at the surface of filamentous phages according to the Winter and Milstein technique (Nature, 1991, 349, 293-299); after several selection steps, the antibody fragments specific for the antigen are isolated and expressed in an appropriate expression system, by conventional cloning and recombinant DNA expression techniques The antibodies or the fragments thereof as defined above are purified by conventional techniques known to those skilled in the art, such as affinity chromatography The antibodies according to the invention are conformational antibodies, i.e. they recognize a conformational epitope or a noncontiguous epitope, or alternatively an assembled topographic epitope, which epitope corresponds to two or more adjacent extracellular domains of the type III membrane proteins, i.e. regions of these type III membrane proteins that are far apart in the primary sequence of the proteins since they are separated by two transmembrane domains and one intracellular domain (FIG. 3, illustrating the example of the EBV LMP1 protein), but that are close when the type III membrane proteins are folded in their native form.

These conformational antibodies recognize the type III membrane proteins only in the native form; they recognize neither the denatured type III membrane proteins, i.e. treated with agents that alter the structure of the proteins, which agents are known to those skilled in the art (methanol, alcohol, acetone, SDS, etc.), nor the fragments of these proteins, in particular the peptides representing a single extracellular domain of said type III membrane proteins.

The antibodies according to the invention that specifically recognize the type III membrane proteins in the native form with high affinity for said native proteins (affinity constant of the order of one nM) represent reliable and sensitive diagnostic reagents for detecting, using a suitable biological sample (whole blood, peripheral blood mononuclear cells, tumor biopsy), patients suffering from latent infections or from pathologies, in particular malignant pathologies, induced by the intracellular pathogenic microorganisms as defined above; these antibodies that specifically recognize the type III membrane proteins in the native form do not require any prior steps consisting of denaturation and/or of cell permeabilization and, optionally, of purification of the infected cells (cell enrichment), before the antibody is brought into contact with the biological sample to be tested. Thus, the antibodies according to the invention can be used for detecting a latency infection, for example by cytometry, by immunocytochemistry or immuno-histochemistry, or else by immunoprecipitation from nonfixed cells (frozen or live) or cells fixed under nondenaturing conditions that are known to those skilled in the art.

A subject of the present invention is also the use of an antibody as defined above, for preparing a diagnostic reagent intended for detecting the latent infections and the associated pathologies as defined above, in particular EBV infections and the associated cancers.

In addition, such conformational antibodies that are capable of specifically lysing the infected cells expressing the type III membrane proteins at their surface are useful in serotherapy, for treating the latent infections, and preventing or treating the associated pathologies, as defined above, in particular EBV infections and the associated cancers.

Consequently, a subject of the present invention is also a pharmaceutical composition, characterized in that it comprises at least one antibody as defined above, combined with at least one pharmaceutically acceptable vehicle.

A subject of the present invention is also the use of the antibodies as defined above, for preparing a medicinal product intended for the treatment of the latent infections and of the associated pathologies as defined above, in particular EBV infections and the associated cancers.

The conformational antibodies according to the invention, directed against the type III membrane proteins, have the following advantages with respect to the existing antibodies:
  simple and rapid use: because of their nature (conformational), the antibodies according to the invention allow direct detection of infected cells in a biological sample without prior steps consisting of denaturation and, optionally, of permeabilization of the cells, or else of purification of the cells (cell enrichment);
  specificity and sensitivity: because of their high affinity for the native type III membrane proteins, the antibodies according to the invention make it possible to specifically and sensitively detect cells infected with the intracellular pathogenic microorganisms as defined above, using a complex biological sample (whole blood, tumor biopsy).

Compared to antitumor chemotherapy and radiotherapy, which are not very specific for their target, or to ex vivo cell immunotherapy, which is specific for each patient but laborious to carry out and expensive, serotherapy using the antibodies according to the invention is relatively inexpensive, simple to use and specific for its target; because of their high cytolytic and pro-apoptotic activities, a limited number of injections per individual will be sufficient to effectively eliminate the infected cells.

In addition, a vaccine composition comprising the antigen according to the invention, coupled to a carrier protein or to a lipid, represents another alternative, that is even less expensive but as effective, for treating latent infections with intracellular pathogenic microorganisms, for example EBV, and preventing or treating the pathologies associated with these infections, in particular cancers.

BRIEF DESCRIPTION OF THE DRAWINGS

Besides the above arrangements, the invention also comprises other arrangements that will emerge from the following description, which refers to examples of use of the antigens and of the antibodies according to the present invention, and also to table I summarizing the sequences of the application, in which the sequences corresponding to the extracellular domains are indicated in bold, the sequences corresponding to the linking fragment are boxed in, and the amino acids derived from the transmembrane domains are underlined, and to the attached drawings in which:

FIG. 1 illustrates the various types of latency (types I, II and III, and optionally type IV) associated with EBV infections; the expression profile of the viral and cellular genes and the pathologies associated with each type of latency are indicated;

FIG. 4 illustrates the lipid vesicles that form spontaneously from the lipopeptides according to the invention: Cys (cholesteryl) derived from the peptides of sequence SEQ ID Nos 13 and 14. A: Coomassie blue staining. B: oil red staining;

FIGS. 8 and 9 illustrate the detection, by immunocytochemistry using the mouse immune sera specific for the LMP1 extracellular domains, of the native LMP1 protein present at the surface of cells having suffered latent infection with EBV. The cells are fixed in PBS buffer containing 4% formaldehyde and the LMP1 protein is detected as described in examples 1.7 and 4;

FIG. 8A illustrates the detection of the native LMP1 protein on lymophoblastoid cell lines transformed with EBV (B.LCL-EBV); all the cells are in type III latency and express LMP1, which is detected on all the cells;

FIG. 8B illustrates the detection of the LMP1 protein on the B95.8 line of B lymphocytes infected with EBV; 40% to 50% of the cells which are in the lytic phase do not express LMP1 (small unlabeled cells), whereas a subpopulation of cells expresses the type III latency antigens, including LMP1 (labeled cells indicated with arrows);

FIGS. 9 (9A, 9B and 9C) illustrates the detection of the native LMP1 protein on PBMCs from healthy, EBV-positive carriers; only a few B lymphocytes are infected and are therefore detectable in these healthy carriers. The detection threshold is at least 1 to 2 LMP1-positive cells per 150 000 to 200 000 PBMCs from healthy EBV-positive carriers;

FIG. 11 illustrates the cytotoxic activity and the pro-apoptotic activity of the mouse immune sera specific for the LMP extracellular domains on a B lymphoblastoid cell line having suffered latent infection with EBV (B.LCL-EBV or LCL). A, C and E: LCLs incubated for, respectively, 4 days in the presence of complement alone [normal rabbit serum (non-immune serum, not heat-inactivated), 1/60$^{th}$ dilution]. B, D and F: LCLs incubated for 4 days in the presence of the same concentration of complement and of increasing concentrations of anti-LPM1 immune serum (1/600$^{th}$, 1/300$^{th}$ and 1/200$^{th}$ dilution). With the LCLs incubated in the presence of complement and with the lowest dilution of anti-LMP1 immune serum (F), considerable cell lysis is observed, which reflects, in terms of the analysis of the cell cycle, a very substantial increase in the proportion of cells in apoptosis (+30%), compared with the control (A, C and E);

TABLE I

Figure 2:
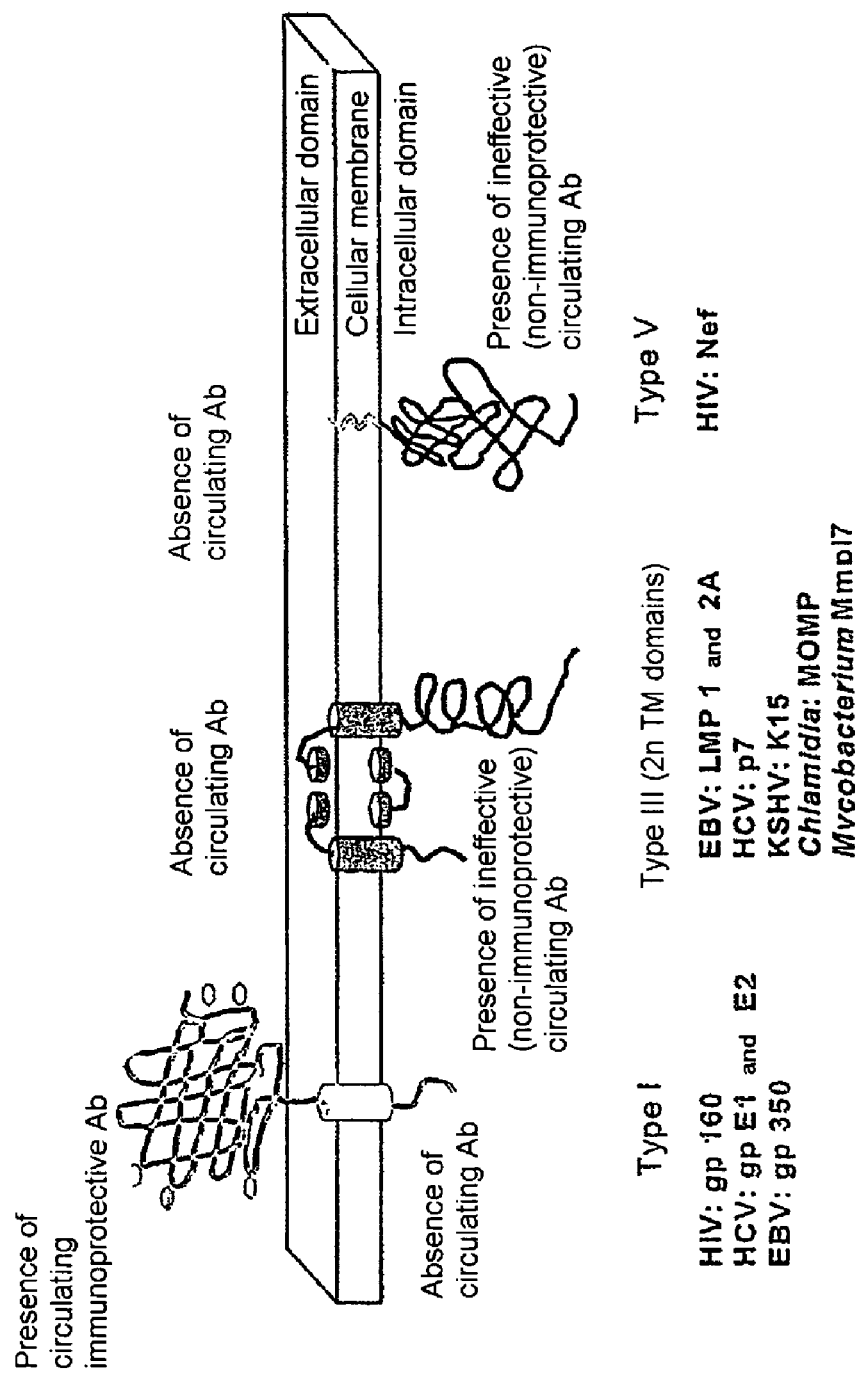
FIG. 2 illustrates the comparative analysis of the structure and of the immunogenicity (presence of protective antibodies) of various types of viral and bacterial membrane proteins (type I: immunogenic and types III and V nonimmunogenic)
Figure 3:
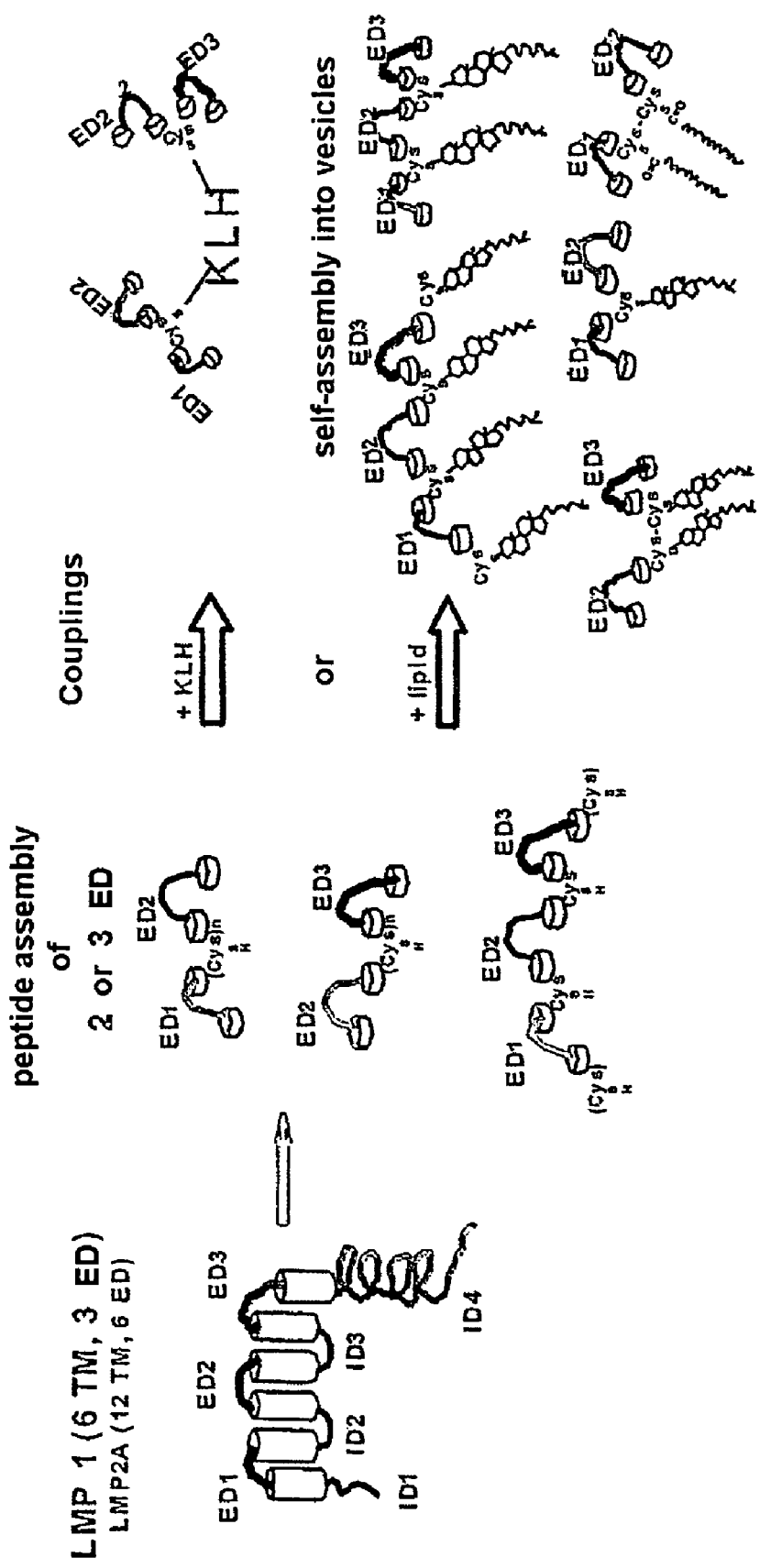
FIG. 3 illustrates the structure of the antigens according to the invention, taking, as an example, those derived from the EBV LPM1 and LMP2A proteins. ED: extracellular domain. TM: transmembrane domain. ID: intracellular domain.

List of the peptides derived from the LMP1 or LMP2 proteins

| Identifier No. | Sequence | Positions | Extracellular Domain (ED) |
|---|---|---|---|
| SEQ ID No: 1 | SDWTGGA | Positions 45 to 51 of LMP1* | LMP1-ED1 |
| SEQ ID No: 2 | WNLHGQA | Positions 98 to 104 of LMP1* | LMP1-ED2 |
| SEQ ID No: 3 | LQQNWN | Positions 160 to 165 of LMP1* | LMP1-ED3 |

TABLE I-continued

List of the peptides derived from the LMP1 or LMP2 proteins

| Identifier No. | Sequence | Positions | Extracellular Domain (ED) |
| --- | --- | --- | --- |
| SEQ ID No: 4 | SCFTASVS | Positions 142 to 149 of LMP2** | LMP2-ED1 |
| SEQ ID No: 5 | RIEDPPFNS | Positions 199 to 207 of LMP2** | LMP2-ED2 |
| SEQ ID No: 6 | DAVLQLS | Positions 260 to 266 of LMP2** | LMP2-ED3 |
| SEQ ID No: 7 | GTLN | Positions 317 to 320 of LMP2** | LMP2-ED4 |
| SEQ ID No: 8 | SILQTNFKSLSSTEFIPN | Positions 374 to 391 of LMP2** | LMP2-ED5 |
| SEQ ID No: 9 | SNTLLS | Positions 444 to 449 of LMP2** | LMP2-ED6 |
| SEQ ID No: 10 | MSDWTGGALCLWNLHGQAL | Positions 44 to 51 and 97 to 105 of LMP1* | LMP1-(ED1 + ED2) |
| SEQ ID No: 11 | LWNLHGQALCLYLQQNWWT | Positions 97 to 105 and 155-166 of LMP1* | LMP1-(ED2 + ED3) |
| SEQ ID No: 12 | MSDWTGGALCLYLQQNWWT | Positions 44 to 51 and 158-166 of LMP1 | LMP1-(ED1 + ED3) |
| SEQ ID No: 13 | CMSDWTGGALCLWNLHGQALC YLQQNWWTC | Positions 44 to 51, 97 to 105 and 159-166 of LMP1* | LMP1-(ED1 + ED2 + ED3) |
| SEQ ID No: 14 | MSDWTGGALCLWNLHGQALCL YLQQNWWT | Positions 44 to 51, 97 to 105 and 158-166 of LMP1* | LMP1-(ED1 + ED2 + ED3) |
| SEQ ID No: 15 | ASSFTASVSTCTWRIEDPPFNSL | Positions 141 to 150 and 197 to 208 of LMP2** | LMP2 (ED1 + ED2) |
| SEQ ID No: 16 | TWRIEDPPFNSLCVDAVLQLSPL | Positions 197 to 208 and 259 to 268 of LMP2** | LMP2 (ED2 + ED3) |
| SEQ ID No: 17 | IVDAVLQLSPLCILGTLNLTTM | Positions 258 to 270 and 317 to 324 of LMP2** | LMP2 (ED3 + ED4) |
| SEQ ID No: 18 | ILGTLNLTTMCGGSILQTNFKSLS STEFIPNL | Positions 315 to 324 and 372 to 392 of LMP2** | LMP2 (ED4 + ED5) |
| SEQ ID No: 19 | GGSILQTNFKSLSSTEFIPNLCV MSNTLLSAW | Positions 372 to 392 and 443 to 451 of LMP2** | LMP2 (ED5 + ED6) |
| SEQ ID No: 20 | ASSFTASVSTCTWRIEDPPFNSL CVDAVLQLSPL | Positions 141 to 150, 197 to 208 and 259 to 268 of LMP2** | LMP2 (ED1 + ED2 + ED3) |
| SEQ ID No: 21 | TWRIEDPPFNSLCVDAVLQLSPL CILGTLNLTTM | Positions 197 to 208 and 259 to 268 and 315 to 324 of LMP2** | LMP2 (ED2 + ED3 + ED4) |
| SEQ ID No: 22 | VDAVLQLSPLCILGTLNLT CGGSILQTNFKSLSSTEFIPNL | Positions 259 to 268 and 315 to 322 and 372 to 392 of LMP2** | LMP2 (ED3 + ED4 + ED5) |
| SEQ ID No: 23 | ILGTLNLTCGGSILQTNFKSLSST EFIPNLCVMSNTLLSAW TWRIEDPPFNSLCVDAVLQLSPL | Positions 315 to 322, 372 to 392 and 443 to 451 of LMP2** Positions 197 to 208 and 259 to 268 of LMP2** | LMP2 (ED4 + ED5 + ED6) LMP2 (ED2 + ED3) |
| SEQ ID No: 24 | VMSDWT | Positions 43 to 48 of LMP1* | LMP1-ED1 |
| SEQ ID No: 25 | NLHGQA | Positions 99 to 104 of LMP1* | LMP1-ED2 |

TABLE I-continued

List of the peptides derived from the LMP1 or LMP2 proteins

| Identifier No. | Sequence | Positions | Extracellular Domain (ED) |
|---|---|---|---|
| SEQ ID No: 26 | LQQN | Positions 160 to 163 of LMP1* | LMP1-ED3 |

*SwissProt P03230
**SwissProt P13285

EXAMPLE 1

Material and Methods

1) Animals

Four week-old female BALB/c mice (Iffa-Credo) are fed at will and immunized at the age of 7 to 10 weeks.

2) Antigens

Peptides derived from the extracellular domains of LMP1 and LMP2A were solid-phased synthesized manually, according to the method originally described by Merrifield et al. (*J. Am. Chem. Soc.*, 1964, 85: 2149-) (1964)), using the Fmoc/tert-Butyl chemistry strategy on a 0.1 mmol scale. The various protected amino acids (Fmoc-L-aa; Novabiochem) are sequentially attached to Rink amide resin (Applied Biosystem) after activation for 3 min with HATU (O-(7-azabenzotriazol-1-yl)-N,N,N',N'-tetramethyluronium hexafluorophosphate), according to the method of Miranda and Alewood (*P.N.A.S.*, 1999, 96: 1881-1186) in the presence of a 5-fold excess of DIEA (diisopropylethylamine). In situ neutralization during the coupling gives better degrees of acylation and in a minimum amount of time. The coupling efficiency is controlled by means of a TNBS (trinitrobenzenesulfonic acid) test. If the test is positive, a second coupling is carried out, followed by an acetylation for 5 min with a 3:0.3:96.7 mixture of $Ac_2$-DIEA-$CH_2Cl_2$, and then by 3 washes for one minute with $CH_2Cl_2$ (chloroform) and then with NMP (N-methylpyrrolidone). The Fmoc protective groups are cleaved before each coupling, with a solution of NMP containing 20% piperidine. At the end of synthesis, the resin is washed with diethyl ether and dried. The peptide is cleaved from the resin and deprotected using a TFA (trifluoroacetic acid)-$H_2O$-EDT-$Pr_3SiH$ mixture (92.5:2.5:2.5:2.5; 15 ml) for 2 hours at ambient temperature, precipitated from cold diethyl ether, centrifuged, washed in cold diethyl ether, recentrifuged, dissolved in water and, finally, lyophilized to give a crude peptide extract. The crude peptide is purified by HPLC on a semi-preparative reverse-phase column (C18 column). The purity of the peptides is always greater than 95% and their identity is confirmed by mass spectrometry (positive MALDI-TOF-MS) and analytical HPLC. The peptide sequences synthesized (SEQ ID Nos 10 to 16) corresponding to the domains of LMP1 (Swiss Protein Databank number P03230) and LMP2A (Swiss Protein Database number P13285) are given in table I in the one-letter-code form.

3) Immunization a) Peptides Coupled to a Carrier Protein (KLH)

The LMP1-derived peptides containing only one exogenous cystein (SEQ ID Nos 10, 11, 12, 15, 16) were individually coupled to activated KLH (Imject maleimide-activated KLH®, Perbio) according to the supplier's protocol. Mice (4 animals per group) were injected subcutaneously in the flank, with an emulsion of peptide (50 µg in 0.1 ml $H_2O$) and of complete Freund's adjuvant (0.1 ml). On days 21, 42 and 62 following the first injection ($D_0$), the animals are given a boost injection, by the same route, with the same amount of antigen but in incomplete Freund's adjuvant. Blood is taken by retro-orbital puncture before each injection, so as to determine the titer of serum antibodies specific for LMP1 and for LMP2A, by ELISA.

b) Peptides Coupled to a Lipid

The LMP1-derived peptides (SEQ ID Nos 10, 11, 13 and 14 were individually coupled to one or more molecules of cholesterol or of palmitic acid, by means of a thioether (cholesterol) or thioester (palmitic acid) bond or bonds with the thiol function of their cysteine residue(s). The coupling of the peptide (5 mg/ml) via a thioether bond to activated cholesterol (bromoacetyl-cholesterol) is spontaneous in a medium of dimethylformamide (DMF)/phosphate buffer, pH 7.5 (95:5). The progression of the reaction is followed by acidification of the reaction medium and an analytical HPLC. The lipopeptide is purified by gel filtration in a 20% acetic acid medium. The palmitic acid is incorporated into the peptide chain by means of a thioester bond, during the peptide synthesis. The lipopeptide organizes itself spontaneously into vesicles (FIG. 4), which are washed by successive centrifugations in an aqueous medium. The mouse immunization protocol is the same as above, except that the Freund's adjuvant is replaced with Montanide®.

4) ELISA

Blood samples are taken, by retro-orbital puncture, from the immunized mice, and the sera are then recovered and frozen at −20° C. in 20-µl fractions. The wells of a microtitration plate (Maxisorp®, Nunc) are coated with 100 µl of peptide (1 mg/ml) overnight at +4° C. Plates coated with non-relevant peptides of the same molecular mass are used as a control. The wells are then washed with PBS buffer containing 0.5% of Tween 20 (PBS-T) and then blocked 1 h in the presence of PBS buffer containing 2% of powdered skimmed milk (PBS-SM). After washes in the same buffer as above, 100 µl of serum diluted in PBS-T-SM buffer (PBS, 0.05% Tween 20, 2% powdered skimmed milk) are added to the wells and the plates are incubated for 2 hours at 37° C. After four washes with PBS-T buffer, 100 µl of goat anti-mouse total immunoglobulins or anti-mouse IgG1, -mouse G2a, -mouse G2b and -mouse G3, secondary antibody, conjugated to peroxydase (BIORAD), diluted to 1/10 000 in PBS-T buffer, are added to each well and the plates are incubated for 1 h at 37° C. After thorough washing with PBS-T buffer, 100 µl of substrate (OPD: o-phenylenediamine dihydrochloride, Sigma) diluted in 0.05 M citrate buffer, pH 5.5, containing $H_2O_2$, are added to each well and the plates are incubated for 30 min at ambient temperature, in the dark. The reaction is stopped by adding 4N sulfuric acid, and the absorption at 492 nm is measured using an automatic microplate reader (Dynatech).

5) Competition Assay

The antigen-antibody binding specificity is measured by means of a competition assay, according to the method described by Friguet et al., (*J. Immunol. Methods*, 1985, 77: 309-309). The principle of the method is as follows: the affinity constants are determined by linear regression from the curves of displacement of the binding of the antibody to the antigen in solid phase (at constant concentration) by varying concentrations of the same antigen in the liquid phase. The first step consists of absorption of the antibody by the antigen or by a non-relevant peptide, in solution, and the second step consists in assaying, by an indirect ELISA assay, free antibodies when the antigen and the antibody are in equilibrium.

More specifically:
  step 1: various concentrations of the peptide antigen or of a non-relevant peptide ($10^{-11}$ to $10^{-5}$ M) are incubated with a fixed concentration of antibodies (serum diluted to $1/50$), in PBS-T-SM buffer (PBS, 2% powdered skimmed milk, 0.05% Tween 20), for 18 h at 4° C.;
  step 2: 100 µl of the product of the reaction obtained in step 1 are sampled and added to the wells of a microtitration plate coated beforehand with the peptide antigen (100 µg/well in NaHCO$_3$ buffer, pH 9.6) and the plate is incubated for 1 h at 20° C. After washes with PBS-T buffer (PBS, 0.05% Tween 20), the immunoglobulins bound to the peptide antigen are detected using a goat anti-mouse total immunoglobulins secondary antibody coupled to peroxydase. The visualization of the reaction and the reading of the plates are carried out as for the ELISA assay.

6) Cell Culture

The human kidney embryonic cell line HEK-293 (ATCC CRL 1573) and the line transfected with the plasmid pSV-HA-LMP1, derived from the HEK-293 line, are cultured in 24-well plates in Dulbecco medium (GIBCO) supplemented with fetal calf serum (10%), glutamine (2 mM), nonessential amino acids (1%), sodium pyruvate (1 mM) and gentamycin (50 µg/ml). The plasmid pSV-HA-LMP1 derives from the plasmid pSV5 (STRATAGENE) through the cloning, under the control of the SV40 virus promoter, of an insert corresponding to the cDNA of LMP1 from the wild-type EBV strain B95.8. The other cells are cultured in RPMI medium supplemented as above. The EBV-infected marmoset B lymphocyte line B95.8 is used for the production of viral particles. The EBV-transformed B lymphocytes (B-EBVneo) and the LCLs (type III-latency EBV+ lymphoblastoidal cell lines) derived from human PMBCs by infection with a culture surnagent of the B95.8 line are obtained as described in *Current Protocols in Immunology*, 1991, Colingan J E, Kruisbeek A M, Margulies D H, Schevach E M, Strober W, Greene. The peripheral blood mononuclear cells (PBMCs) are purified by centrifugation of a blood sample on a Ficoll gradient. The human T lymphocytes Jurkat line and the EBV-negative Burkitt's lymphoma DG75 line are also used as controls.

7) Immunocytochemistry

The experiments are carried out on coverslips (cells in suspension) or in 24-well plates (adherent cells) using conventional immunocytochemistry techniques, employing a standard ABC protocol. More specifically, the adherence cells cultured in plates and the nonadherence cells cultured in suspension are washed with PBS, and then, only in the case of the cells in suspension, deposited onto a coverslip (100 µl at $10^6$ cells/ml). The cells are then fixed (plates or coverslips) under nondenaturing conditions: incubation for 30 min in PBS buffer containing 4% formaldehyde, and then three washes for 1 min with PBS and, finally, blocking with 4% H$_2$O$_2$. In parallel, the cells are fixed under denaturing conditions: incubation for 30 min in PBS buffer containing 4% formaldehyde, and then denaturation by dehydration with increasing concentrations of ethanol (50°, 70°, 90° and 100°) and, finally, blocking with 4% H$_2$O$_2$.

The incubations with the primary and secondary antibodies are carried out either in PBS buffer containing 5% of powdered skimmed milk (cells fixed under nondenaturing conditions), with neither detergent nor any organic compound capable of inhibiting the binding of the antibody, or in PBS buffer containing 0.5% of Tween 20 or 0.05% of saponin (cells fixed under denaturing conditions). More specifically, the cells are first incubated for 45 min at ambient temperature, in the presence of a mouse immune serum specific for LMP1, prepared as described in example 1 and in example 2 (dilution to $1/1000^{th}$) and of a normal rabbit serum (dilution to $1/300^{th}$). The mouse antibodies are then labeled with a biotinylated rabbit antibody (SIGMA), according to the supplier's recommendations. After three washes with PBS, the biotine attached is detected using a peroxydase-coupled ABC enzymatic system (Axtravidin, SIGMA) and the reaction is then visualized with diaminobenzidine (SIGMA).

8) Analysis of proliferation and of the cell cycle

An EBV-infected lymphoblastoidal cell culture (LCLs, $10^6$ cells/ml) is distributed into a 6-well plate ($10^6$ cells/well) and the cells are then incubated for 4 days in RPMI medium containing non-decomplemented normal rabbit serum (dilution to $1/60^{th}$). Alternatively, the cells are incubated for 4 days with non-decomplemented normal rabbit serum at the same concentration and increasing concentrations of anti-LMP1 mouse immune serum (dilutions to $1/600^{th}$, $1/300^{th}$ and $1/200^{th}$) prepared as described in examples 1.3 and 2.

The cell proliferation is analyzed by direct observation of the cultures (number of cells and cell morphology) under an optical microscope.

For the cell cycle analysis, 1 ml of cells are removed at $D_4$, rinsed in PBS, fixed in PBS buffer containing 4% formaldehyde for 30 min at 4° C., washed twice in cold PBS buffer, and then centrifuged. The cell ??? obtained is resuspensed in 1 ml of PBS buffer containing 200 µg of propidium iodide and 100 µg of RNase A (/ml), and then incubated for 30 min at 37° C. The reactions are kept at 4° C. overnight and the DNA content of the cells is then analyzed by fluorometry (EPICS-XL cytometer, Coulter) so as to determine the percentage of cells in $G_0/G_1$ (2n), S (>2n and <4n) and $G_2/M$ (4n) phase, and undergoing apoptosis (<2n).

9) Immunoprecipitation $10^6$ HEK-293 cells are transfected with the plasmid pSV-HA-LMP1 or with the control plasmid pSV5, using polyethyleneimine, under the conditions recommended by the supplier. 48 hours after transfection, the cells are rinsed twice with PBS buffer, and lysed for 15 min on ice, in 500 µl of PY buffer (20 mM Tris HCl, pH 7.4, 50 mM NaCl, 5 mM EDTA and 1% Triton X-100) supplemented with protease inhibitors (1 mM leupeptin, 1 mM sodium orthovanadate and 5 IU/µl of aprotinin), and the lysate is then, finally, clarified by centrifugation at 14 000 rpm. The lysate thus obtained is incubated for one hour at +4° C. with gentle agitation, with a murin monoclonal antibody that recognizes an intracellular region of LMP1 (CS1-4, Novocastra) or with 5 µl of anti-LMP1 mouse immune serum prepared as described in examples 1.3 and 2. 100 µl of a solution of protein A-sepharose (Amersham-Pharmacia) are then added and the mixture is gently agitated on a turntable, for one hour at +4° C. The sepharose beads are then washed four times with PY buffer, eluted with 30 µl of Laemmli buffer and then subjected to polyacrylamide gel electrophoresis in the presence of SDS (SDS-PAGE).

After the electrophoretic separation, the proteins present in the gel are then transferred onto membranes (Immobilon-P, Millipore) by electro-blotting. The membranes are saturated for 1 and a half hours with a solution of casein (0.2%) in PBS buffer-0.1% Tween 20, and are then incubated for one hour with the CS1-4 murin antibody. After successive washes, the membranes are incubated for 15 minutes with peroxydase-conjugated anti-mouse IgG immunoglobulins (Jackson Immunoresearch) and the LMP1 protein immunoprecipitated is visualized using the ECL kit (Amersham).

EXAMPLE 2

Preparation of Conformational Antibodies Directed Against the Extracellular Domains of the EBV LMP1 Protein Antibodies directed against the extracellular domains of the EBV LMP1 protein were prepared by immunization of mice with the peptides SEQ ID Nos 10 and 11 coupled to KLH, or else with the peptide SEQ ID No. 13 coupled to cholesterol, as described in example 1. The kinetics of appearance of the serum antibodies directed against the extracellular domains of the LMP1 protein were analyzed by ELISA, as described in example 1.

Figure 5:
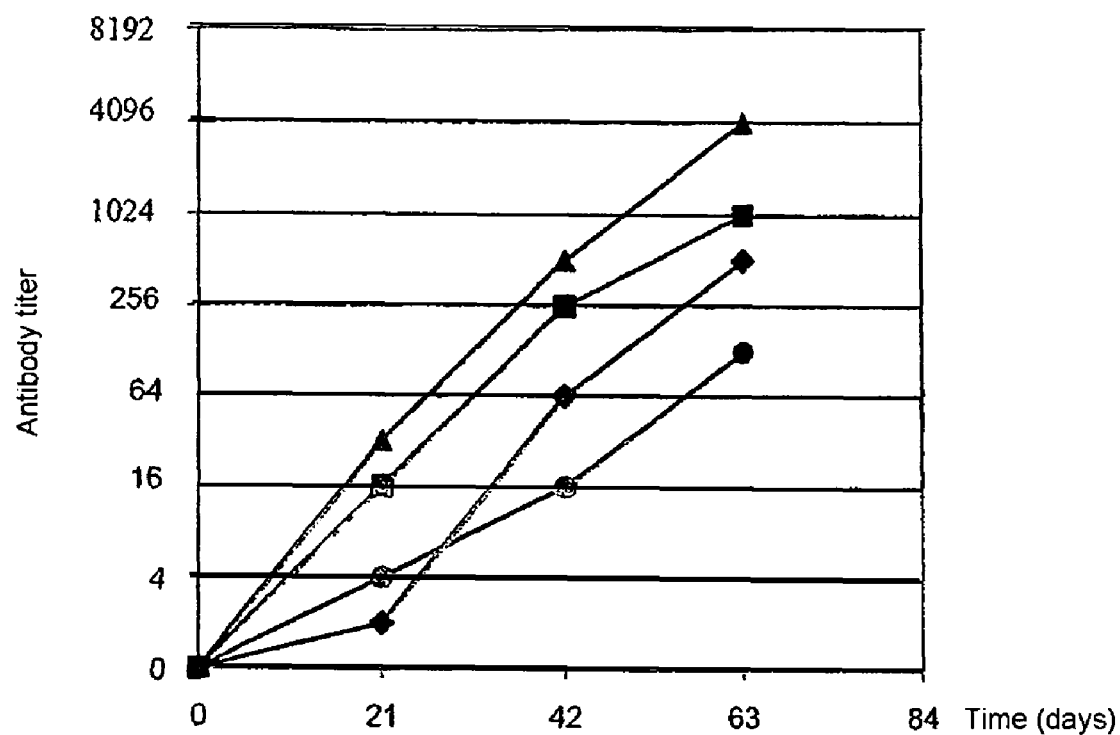
FIG. 5 illustrates the evolution of the anti-LMP1 serum antibody titer in 4 mice (mouse 1 to mouse 4) immunized with the peptide antigen SEQ ID No. 10 (ED1+ED2 of LMP1) coupled to KLH; the serum antibodies were assayed by ELISA with the corresponding peptide (SEQ ID No. 10), on days $D_{21}$, $D_{42}$, $D_{63}$ and $D_{84}$, i.e. three weeks after each of the 4 successive injections of antigen: mouse 1: —◇—, mouse 2: ———; mouse 3: —△—, mouse 4: —○—.

The results illustrated in FIG. 5 and in table II show that the antigens according to the invention are immunogenic, i.e. they induce the production of antibodies directed against the extracellular domains of the LMP1 protein when they are administered in vivo to an individual.

TABLE II

Immunogenic potency of the antigens

| Peptide | Sequence | Identifier Number | Immunogenic Potency |
|---------|----------|-------------------|---------------------|
| LMP1 Domain 1 + 2 | MSDWTGGALCLWNLHGQAL | SEQ ID No: 10 | +++ |
| Domain 2 + 3 | LWNLHGQALCLYLQQNWWT | SEQ ID No: 11 | +++ |
| Domain 1 + 3 | MSDWTGGALCLYLQQNWWT | SEQ ID No: 12 | - |
| Domain 1 + 2 + 3 | CMSDWTGGALCLWNLHGQALCYLQQNWWTC | SEQ ID No: 13 | +(IgM) |
| Domain 1 + 2 + 3 | MSDWTGGALCLWNLHGQALCLYLQQNWWT | SEQ ID No: 14 | +(IgM) |

EXAMPLE 3

Analysis of the Specificity and of the Affinity of the Anti-LMP1 Antibodies

The specificity and the affinity of the antibodies produced as described in examples 1 and 2 are measured using the competition assay, as described in example 1.

Figure 6:
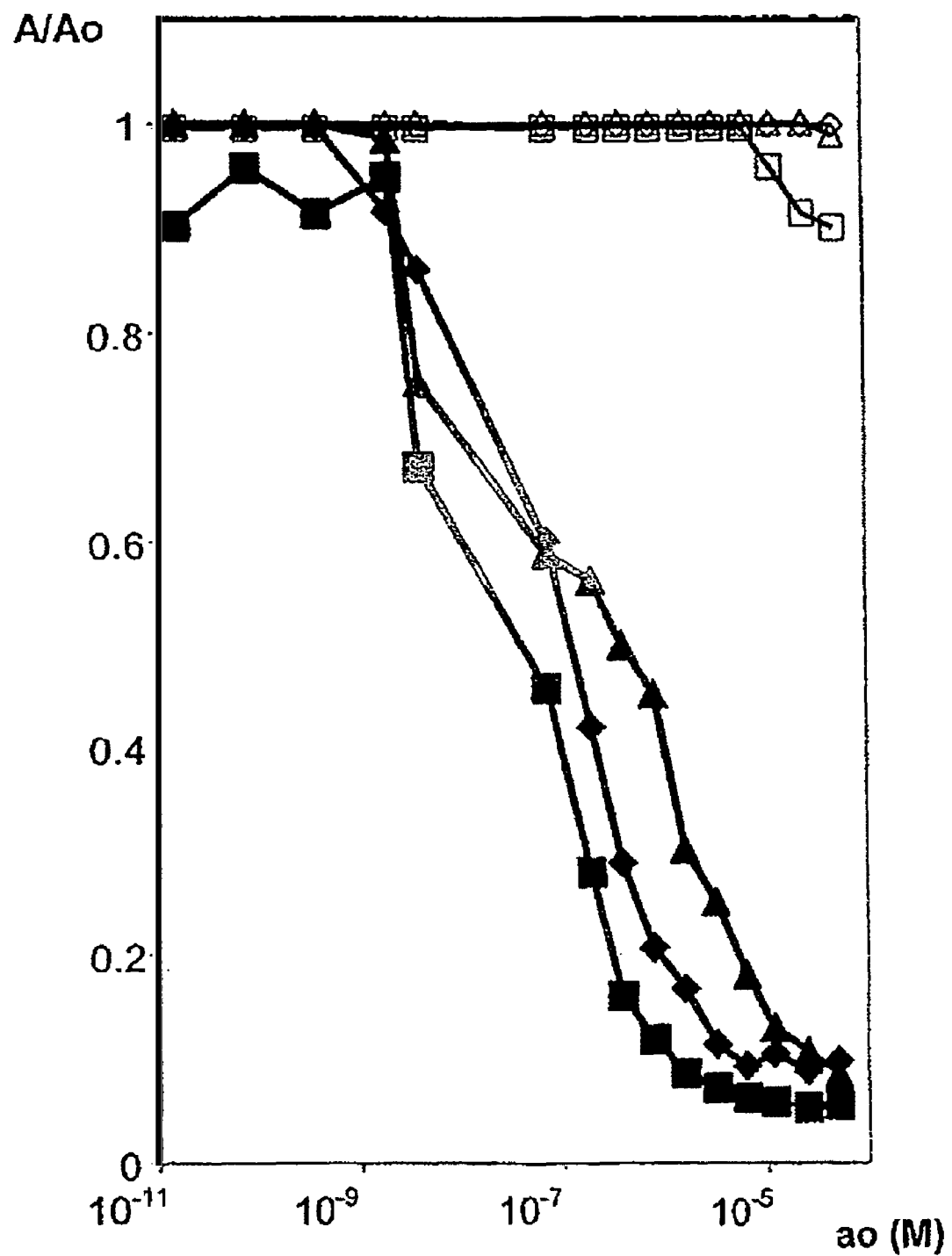
FIG. 6 illustrates the analysis of the specificity of the anti-LMP1 mouse immune sera (mouse immunized with the peptide antigen SEQ ID No. 10 (ED1+ED2) coupled to KLH), measured by indirect ELISA, by competition assay with the corresponding peptide (SEQ ID NO. 10) or with a non-relevant peptide (SEQ ID No. 12, ED1+ED3). The results are expressed, for each of the sera taken at D21 (3.1), D42 (2.1) and D63 (1.1), by the ratio (A/AO) of the absorbent values in the presence or in the absence of competitor peptide, as a function of the molar concentration ($a_o$) of the competitor peptide (ED1+ED2) or (ED1+ED3). Competition with the peptide SEQ ID No. 10: 3.1: —■—, 2.1: —◆— and 1.1: —⊕—. Competition with the peptide SEQ ID No. 12: 3.1: —-☒-,—, 2.1: -♪-and 1.1: —△—.
Figure 7:
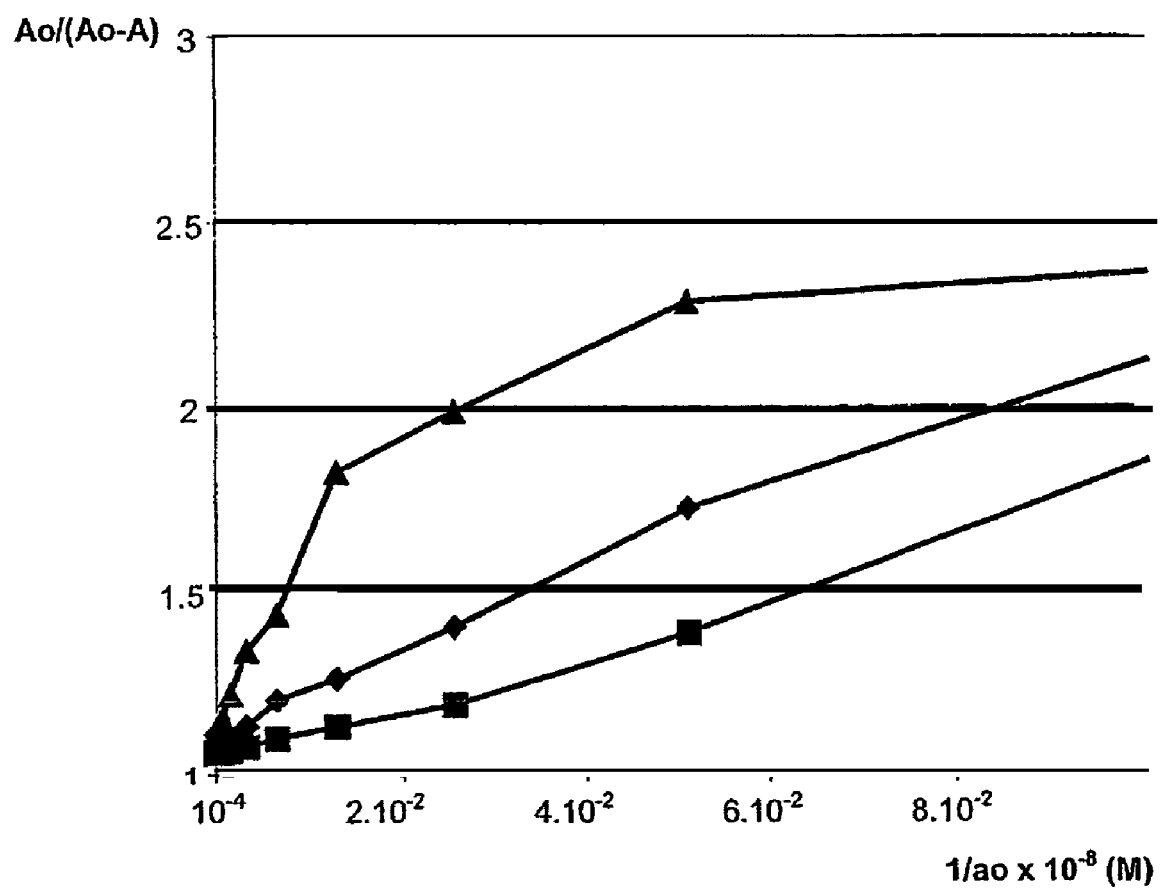
FIG. 7 illustrates the determination, by linear regression from the curve of FIG. 6, of the affinity constant ($K_a$) of the antibodies of the anti-LMP1 mouse immune sera. The Ka values correspond, respectively, to 7.3 nM, 20.8 nM and 557 nM for the sera 3.1 (—■—), 2.1 (—♦—) and 1.1: (—⊕—)

The results obtained with the antibodies directed against the antigen representing the concatenation of the extracellular domains ED1 and ED2, separated by a cysteine residue (antigen (ED1+ED2), SEQ ID NO. 10), are illustrated respectively in FIGS. 6 and 7.

The absence of competition with the peptide (ED1+ED3) demonstrates:

firstly, that the antibodies recognize the antigen (ED1+ED2) specifically (FIG. 6), and secondly, since these antibodies, that are polyclonal in nature (immune serum), show no reactivity with the peptide ED1+ED3, which has the ED1 sequence in common with the antigen (ED1+ED2), these results also indicate that the antibodies are conformational antibodies, given that they specifically recognize a noncontiguous epitope corresponding to the extracellular domain 1 combined with the extracellular domain 2, which domains are far apart in the primary sequence of the proteins since they are separated by a transmembrane domain and an intracellular domain, but are close when the LMP1 protein is folded in its native form.

The affinity constants determined by linear regression from the curve of FIG. 6, show that immunization with the antigen (ED1+ED2) makes it possible to produce antibodies that have a high affinity for the antigen (Ka of 7.3 nM and 20.8 nM).

EXAMPLE 4

Analysis of the Reactivity of the Antibodies with Respect to the Native or Denatured LMP1 Protein The reactivity of the mouse immune sera prepared as described in examples 1.3 and 2, with respect to the native or denatured LMP1 antigen, is tested by immunocytochemistry, as described in example 1.7. Alternatively, the reactivity of the sera is tested by Western blotting (denaturing conditions), according to standard protocols known in themselves or by immunoprecipitation (native conditions), as described in example 1.9.

Figure 10:
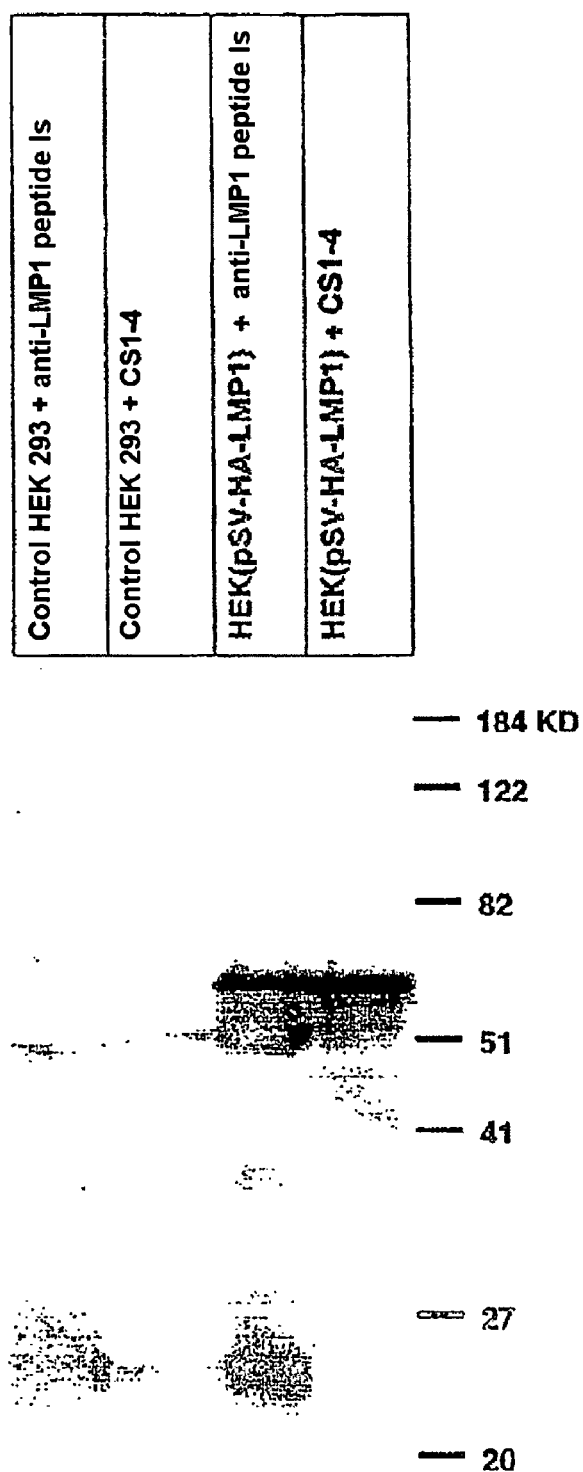
FIG. 10 illustrates the detection by immunoprecipitation of the native LMP1 protein in HEK-293 cells transfected with a vector for expression of the LMP1 protein (pSV-HA-LMP1), using the mouse immune sera specific for the LMP1 extracellular domains according to the invention (anti-peptide Is), by comparison with a commercial mouse monoclonal antibody that recognizes an intracellular domain of LMP1 (CS1-4). HEK-293 cells transfected with the vector pSV5 are used as a control (control HEK 293). Lane 1: control HEK 293 on which immunoprecipitation is performed with the anti-LMP1 mouse immune serum. Lane 2: control HEK 293 on which immunoprecipitation is performed with the CS1-4 antibody. Lane 3: HEK 293 transfected with pSV-HA-LMP1, on which immunoprecipitation is performed with the anti-LMP1 mouse immune serum. Lane 4: HEK 293 transfected with pSV-HA-LMP1, on which immunoprecipitation is performed with CS 1-4 antibody. The positions of the molecular weight markers are indicated.

The results illustrated in FIGS. 8, 9 and 10 demonstrate that the mouse immune sera contain conformational antibodies that sensitively and specifically recognize the native LMP1 protein expressed at the surface of cells from patients suffering from latent infection with EBV, by immunocytochemistry (cells fixed under nondenaturing conditions as specified in example 1.7) and by immunoprecipitation (cell lysates prepared under nondenaturing conditions); on the other hand, they do not recognize the LMP1 protein in the denatured form, by immunocytochemistry (cells fixed under denaturing conditions as described in example 1.7) and by Western blotting (cell lysates prepared under denaturing conditions).

EXAMPLE 5

Analysis of the Cytotoxicity of the Antibodies (ADCC)

The cytotoxicity of the antibodies is tested on B lymphoblastoidal lines having suffered latent infection with EBV (B-LCLs), incubated with complement, alone (control) or in the presence of anti-LMP1 mouse immune serum, as described in example 1.8.

The results show that the anti-LMP1 immune sera have ADCC-type cytotoxicity, with respect to the cells having suffered latent infection with EBV:

direct observation of the B-LCLs shows that, at 24 h, 50% of the cells incubated in the presence of complement and of the lowest dilution of immune serum were lysed; at later times, lysis of all the cells is observed;

the cell cycle analysis (FIG. 11) shows that, after 4 days, 50% of the B-LCLs incubated in the presence of complement and of the lowest dilution of immune serum are undergoing apoptosis (F); by comparison with the control cells incubated in the presence of complement alone (A, C and E), a clear decrease in cell proliferation (decrease in the proportion of cells in S and G2/M phases), and a 30% increase in the proportion of cells undergoing apoptosis, are observed with these same B-LCLs incubated in the presence of complement and of the lowest dilution of immune serum.

EXAMPLE 6

Preparation of Conformational Antibodies Directed Against the Extracellular Domains of the EBV LMP2A Protein Antibodies directed against the extracellular domains of the LMP2A proteins were prepared by immunization of batches of 4 BALB/c mice or of batches of 3 LOU/M rats with the peptides SEQ ID Nos 15, 16 and 17 coupled to activated KLH as described in example 1. The response in terms of antibodies directed against the extracellular domains of the LMP2A protein was analyzed by ELISA, as described in example 1.

The results given in table III show that the antigens according to the invention exhibit a high immunogenic potency (symbolized by + signs), comparable to that of the antigens derived from the extracellular loops of LMP1 (example 2). The best humoral response was developed against the peptide SEQ ID No. 16 (table III). The peptides SEQ ID Nos 18 and 19 were not synthesized.

TABLE III

Immunogenic potency of the LMP2A antigens in mice (BALB/c) and rats (LOU/M)

| LMP2A | Sequences synthesized | SEQ ID No. | Immuno-genic Potency |
|---|---|---|---|
| loop ED1 + ED2 | ASSFTASVSTCTWRIEDPPFNSL | 15 | ++ |
| loop ED2 + ED3 | TWRIEDPPFNSLCVDAVLQLSPL | 16 | +++ |
| loop ED3 + ED4 | IVDAVLQLSPLCILGTLNLTTM | 17 | ++ |
| loop ED4 + ED5 | ILGTLNLTTMCGGSILQTNFKSLSSTEFI PNL | 18 | NT |
| loop ED5 + ED6 | GGSILQTNFKSLSSTEFIPNLCVMSNTLL SAW | 19 | NT |

*NT: not tested

EXAMPLE 7

Analysis of the Specificity and of the Affinity of the Anti-LMP2A Antibodies

The specificity and the affinity of the anti-LMP2A antibodies produced as described in example 6 were measured using the competition assay described in example 1.

Figure 12:
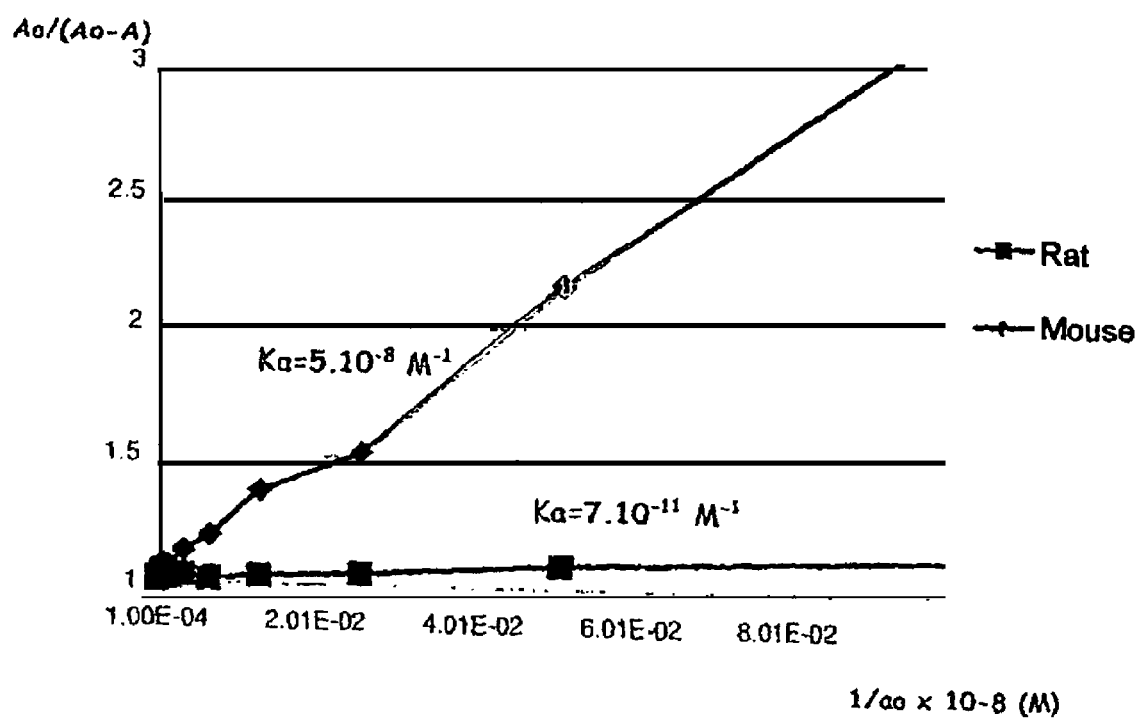
FIG. 12 illustrates the comparison of the mean affinities of the mouse (BALB/c) and rat (LOU/M) immune sera after three booster immunizations with the peptide antigen SEQ ID No. 16 (ED2+ED3 of LMP2A) coupled to KLH.

The mean affinity of the antibodies produced in BALB/c mice and LOU/M rats immunized with the peptide SEQ ID No. 16 is illustrated in FIG. 12, which is representative of the results obtained with the three peptides tested (SEQ ID Nos 15, 16 and 17). Immunization with the LMP2A antigens makes it possible, after three boosters, to produce antibodies having, in mice, an average affinity (FIG. 12, Ka=50 nM$^{-1}$) less than that obtained with the peptides derived from the extracellular loops of LMP1 (FIG. 7, Ka=7.3 nM$^{-1}$). Comparative analysis of the affinity, after 3 immunizations, of the antibodies against extracellular loops ED2+ED3 of LMP2A produced in rats and mice shows that the antibodies produced in rats have a much higher affinity than those produced in mice (FIG. 12; Ka=7×10$^{-11}$ M$^{-1}$ in rats versus 5×10$^{-8}$ M$^{-1}$ in mice). Similar results are obtained with the mouse and rat antibodies produced with respect to the LMP1 peptides.

The anti-LMP2 rat immune sera will be used in the studies of in vivo serotherapy of EBV-positive human tumors induced in SCID mice.

EXAMPLE 8

Analysis of the Reactivity of the Anti-LMP2A Antibodies with Respect to the Native Protein 1) Materials and Methods a) Construction and Production of an Expression Vector for LMP2A (pREP4-LMP2)

The LMP2A cDNA was amplified by RT-PCR from mRNA extracted from EBV-positive lymphoblastic cells (LCLs). The pair of primers used for the PCR (SEQ ID No. 27: 5'AGAATTCATGGGGTCCCTAGAA3' and SEQ ID No. 28: 5'AGGTACCTTATAGAGTGTTGCGA3') contain, in bold, the EcoR1 and KpnI restriction sites for insertion into the TOPO plasmid, and, underlined, the sequences complementary to the LMP2A (strain B95.8) cDNA.

Competent JM 109 bacteria (Invitrogen) were transformed, by thermal shock, with the plasmid TOPO-LMP2A, and were then amplified for one hour at 37° C. and selected overnight at 37° C. on Luria Broth Base agar medium (LB, Invitrogen) supplemented with ampicillin (Appligene) and with X-Gal (Eurogentec). Positive clones possessing the LMP2 cDNA insert (1 500 bp) were isolated by enzymatic digestion and agarose gel electrophoresis of plasmid DNA minipreparations. These positive clones were then amplified overnight at 37° C. in 30 ml of liquid LB supplemented with ampicillin, overnight at 37° C., and the plasmid TOPO-LMP2 was then extracted using the Nucleobond AX kit, according to the supplier's protocol (Machery Nagel). The plasmid DNA thus obtained was quantified by specrophotometry at 260 nm and verified by enzymatic digestion and 1.5% agarose gel electrophoresis in the presence of ethidium bromide.

The plasmid TOPO-LMP2 (20 μg) was digested with HindIII and NotI (Roche Diagnostic) and the LMP2A insert (1 500 pb) was then isolated by agarose gel electrophoresis and purified using the Nucleospin Extract kit (Machery Nagel). 45 ng of insert were added to 100 ng of pREP4 linearized by digestion with HindIII and NotI, and the mixture was then ligated with 2 IU of T4 phage ligase (Promega) overnight at 4° C. Competent bacteria were then transformed with the ligation product. Positive clones (pREP4-LMP2A) were isolated and amplified as above for the plasmid TOPO-LMP2A.

b) Stable Transfection of Cell Lines with the Expression Vector pREP4-LMP2A

The reactivity of the anti-LMP2A antibodies produced, with respect to the native LMP2A protein, was tested using a cell line stably transfected with the plasmid pREP4-LMP2A, obtained in the following way:

HEK 293 cells were seeded into 6-well plates, in 2 ml of DMEM medium supplemented with 10% FCS (DMEM-10% FCS) and then cultured until a cell culture in the exponential phase was obtained. The cells were then rinsed and incubated in 1 ml of Optimem (GIBCO), to which a mixture of plasmid pREP4 or pREP4-LMP2A (1 to 2 ug of total DNA) and of PEI (polyetheleneimine, 4 μl/ug of DNA, Euromedex) was added as transfecting agent. After incubation for 5 hours, the transfection medium was replaced with 2 ml of DMEM-10% FCS medium. Cells stably expressing LMP2A were selected by culturing in the presence of 100 μg/ml of hygromycin for 4 to 5 weeks.

The expression vector used (pREP4) can persist stably in episomal form in the transfected cells, by virtue of its Ori P origin of replication. It replicates synchronously with division and is therefore, theoretically, entirely transmitted to all the daughter cells. A new cell line expressing LMP2A (HEK-LMP2A) is obtained, which can be compared with the HEK line of origin in immunocytochemistry assays.

c) Anti-LMP2 Immunocytochemistry on HEK and HEK-LMP2A Cells

The HEK 293 or HEK-LMP2 cells are suspended (100 000 ml) by digestion with a trypsin solution for 15 min at 37° C., and then washing in PBS buffer. The cells are deposited onto a histological slide, completely dried, and then rehydrated and fixed under nondenaturing conditions: incubation in PBS buffer containing 4% paraformaldehyde, for 20 min at ambient temperature. After washing with PBS, the cells are treated with 3% aqueous hydrogen peroxide for 10 min and saturated with blocking buffer (PBS-5% powdered skimmed milk). The cells are then incubated with the anti-LMP2 rat immune serum prepared as described in example 6 (1/500) saturated with normal goat serum (1/50). The rat IgGs are detected using the Extra5 detection-amplification kit (Sigma) and the presence of exogenous peroxydase is visualized by means of diaminobenzidine for 5 to 10 min, depending on the intensity of the coloration.

2) Results

Figure 13:
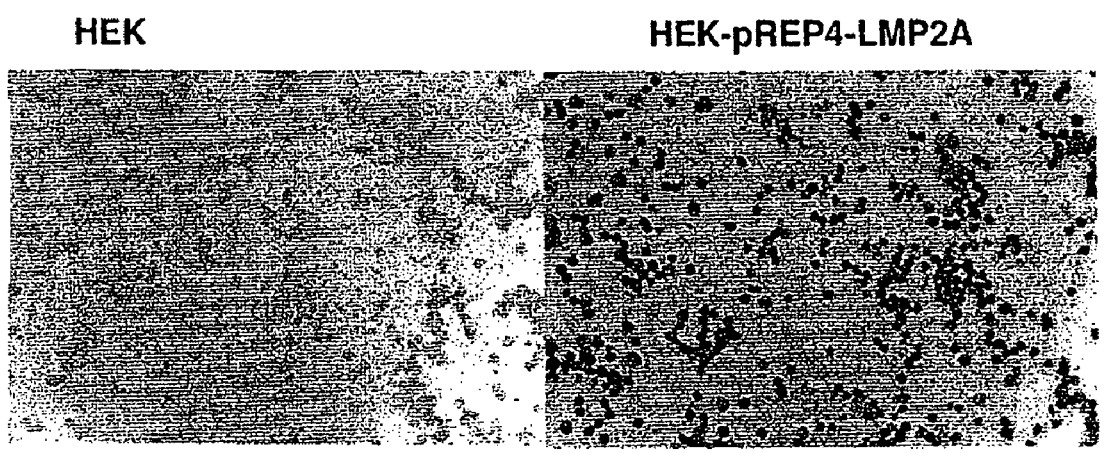
FIG. 13 illustrates the detection, by immunocytochemistry using rat immune sera specific for the extracellular domains of LMP2A, of the native LMP2A protein present at the surface of an HEK-293 line stably transfected with the expression vector pREP4-LMP2A. The cells are fixed in PBS buffer containing 4% formaldehyde and the LMP2A protein is detected as described in example 8.

FIG. 13 shows that the rat anti-LMP2 antibodies specifically recognize the LMP2A protein expressed at the membrane of the cells transfected with the expression vector pREP4-LMP2A; in these cells, very extensive labeling (brown coloration) is observed with the rat anti-LMP2 antibody, whereas the cells of the line of origin, which differ only by the absence of expression of LMP2A, are not labeled with the anti-LMP2 antibodies. The detection of the LMP2A protein with the rat anti-LMP2 antibodies is carried out without prior permeabilization of the cells, demonstrating that the antibodies are capable of binding specifically to the LMP2A protein expressed at the membrane of the transfected cells.

EXAMPLE 9

Antitumor Serotherapy and Immunization Using the Anti-LMP1 and Anti-LMP2 Antibodies and Antigens The antitumor serotherapy experiments using the anti-LMP2A antibodies were carried out in a human tumor model in SCID (Severe Combined Immunodeficiency) mice. The antitumor immunization experiments were carried out in BALB/c mice, with peptide antigens and transfected murin tumor cells.

1) Serotherapy a) Induction of Tumors Expressing LMP1 and LMP2A in SCID Mice

EBV+ human cell lines of monocyte origin (E1) and T lymphocyte origin (NC5), that develop a latency II EBV phenotype (Masy E, et al., *J. Virol.*, 2002, 76: 6460-72; FIG. 1), are tumorigenic in SCID mice. The E1 and NC5 cells are cultured in DMEM-10% FCS medium and maintained in the exponential growth phase by adding fresh medium. The cells in suspension are washed twice in PBS by centrifugation and diluted to 10 or 30 million/ml in 0.9% NaCl medium, and then injected subcutaneously into the interscapular region in SCID mice (0.1 ml per mouse). The mice are sacrificed when the interscapular tumor exceeds 250 mm². The survival results for the mice injected with the two amounts of cells (1 million or 3 million) of each of the lines are given in table IV.

TABLE IV

Influence of the number and of the type of cells injected on the survival of SCID mice

| Number of cells | E1 cells | NC5 cells | % survival |
| --- | --- | --- | --- |
| 1 million | + | − | 42 (n = 12) |
| 3 million | + | − | 25 (n = 9) |
| 1 million | − | + | 33 (n = 9) |
| 3 million | − | + | 16 (n = 6) |

The cells (E1 or NC5) gave palpable tumors from the beginning of the second week following injection in most of the mice, which had to be sacrificed before the end of the third week of the experiment.

Of the two cell types tested, the NC5 cells are the most aggressive (table IV). Some SCID mice did not exhibit any tumors more than 45 days after the injection, which justifies a certain survival percentage in table IV.

b) Verification of the Expression of LMP1 and LMP2A at the Surface of the E1 and NC5 Cells The presence of LMP1 and LMP2A at the surface of the E1 and NC5 cells was controlled by immunocytochemistry, using anti-LMP2A rat immune serum, anti-LMP1 mouse immune serum and normal serum (NRas), according to the protocols described in examples 1.7 and 8.

Figure 14:
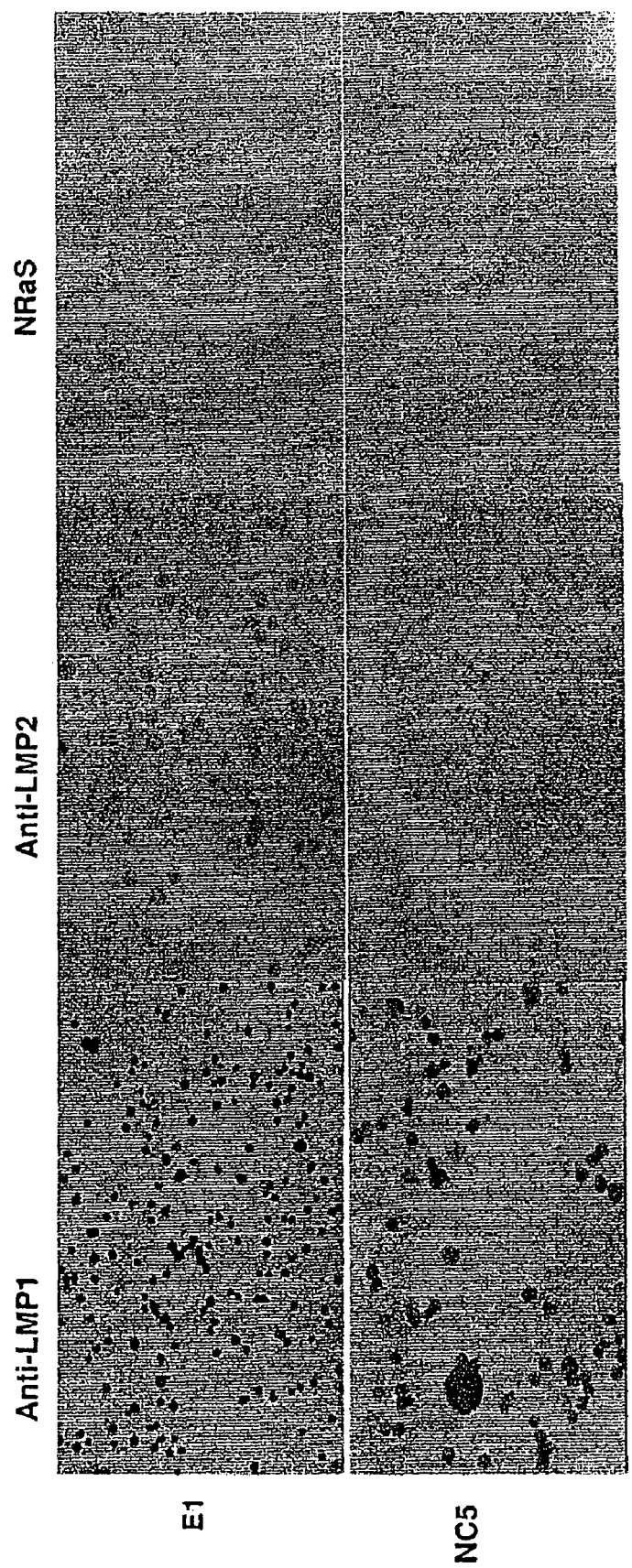
FIG. 14 illustrates the detection, by immunocytochemistry using immune sera specific for the extracellular domains of LMP1 and LMP2A, of the native LMP1 and LMP2A proteins present at the surface of the EBV+E1 and NC5 lines. The cells are fixed in PBS buffer containing 4% formaldehyde and the LMP1 and LMP2A proteins are detected as described in examples 1.7, 4 and 8 (magnification: ×400)

The intensity of the LMP1 labeling is much greater than that for LMP2A on the two cell types (FIG. 14), in agreement with a high expression level for LMP1 and LMP2A. The LMP2A labeling on the NC5 cells is even very slight, compared with that of LMP2A on the E1 cells, but clearly greater than the background noise (NRaS column, FIG. 14).

c) Anti-LMP2 Antitumor Serotherapy

The studies of serotherapy for tumors induced in SCID mice were carried out on E1 cells with the rat anti-LMP2A antibodies having an affinity of $7 \times 10^{-11}$ $M^{-1}$, described in examples 6 and 7 and in FIG. 12, directed against the peptide (SEQ ID No. 16) that mimics the ED2+ED3 domains of LMP2.

Four groups of 10 SCID mice were given an interscapular subcutaneous injection of 3 million E1 cells in a volume of 100 μl of 0.9% NaCl, on the same day, from the same preparation of E1 cells. On D+2 and D+5 after injection, the three groups of 10 mice were given two intraperitoneal (i.p.) injections of 40 μl of rat anti-LMP2 antibodies diluted in 100 μl of 0.9% NaCl, while the control group was given 100 μl of normal rat serum.

Figure 15:
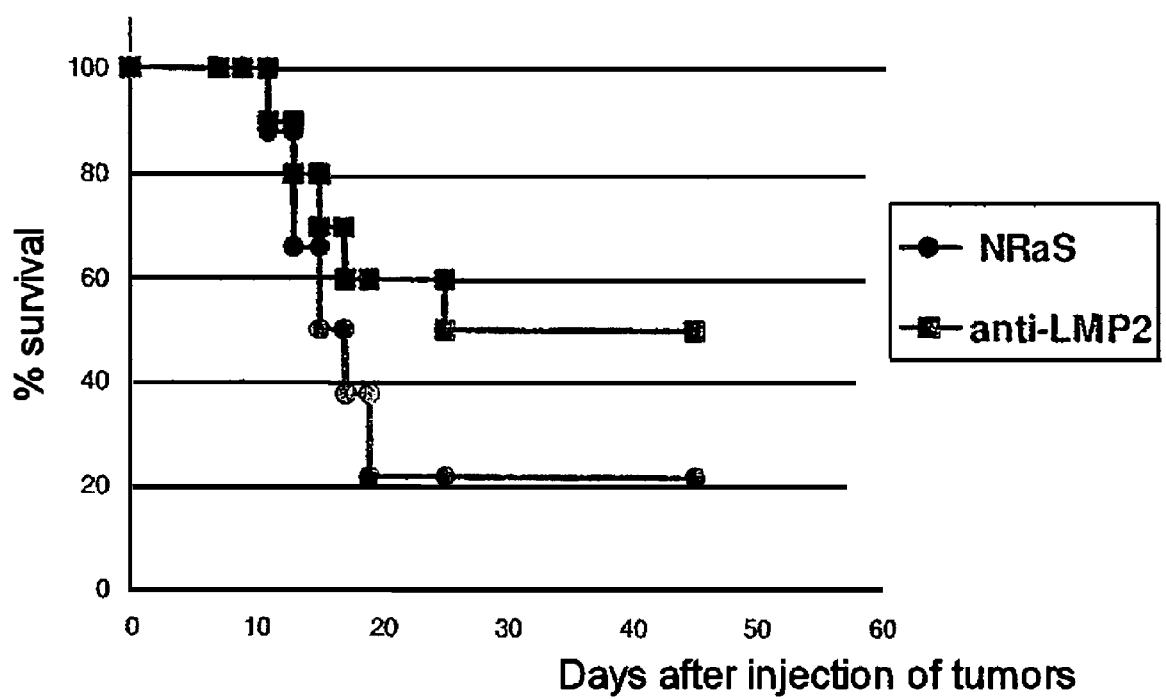
FIG. 15 represents the survival curve of SCID mice injected with 3 million E1 cells, and then treated with an anti-LMP2A serum or a normal serum.

The survival curve for the SCID mice injected with 3 million E1 cells, and then treated with anti-LMP2A serum or a normal serum, is given in FIG. 15. Only 22% of the control mice survive with an injection of normal rat serum (NRaS), in agreement with the data in table IV showing 25% survival for the SCID mice injected with 3×10⁶ E1 cells and having undergone no particular treatment. On the other hand, the SCID mice injected with 3 million E1 cells and treated with two injections of 40 µl of anti-LMP2 antibodies exhibit delayed tumor progression, and 50% of them are protected for at least 45 days, with respect to the appearance of tumors (FIG. 15).

These results demonstrate that the anti-LMP2 extracellular loop antibodies are capable of preventing the appearance and the development of human tumors induced by E1 cells in SCID mice.

2) Preventive Anticancer Immunization

These experiments comprise: (i) immunization of BALB/c mice (immunocompetent) with the LMP1 antigen so as to obtain conformational antibodies against LMP1 extracellular loops, and (ii) inoculation of the tumorigenic cells of murin origin.

a) Production of a Tumorigenic Line Expressing LMP1

Firstly, a tumorigenic murin line stably expressing LMP1 was constructed in a manner similar to the line expressing LMP2A described in example 8.

Construction of the Plasmid pREP4-LMP1

The LMP1 cDNA was isolated by digestion of the plasmid pSVHA-LMP1 using the HindIII and NotI restriction enzymes, and then cloned into the same sites in the plasmid pREP4, as described in example 8.

Production of a Stable Line Expressing LMP1

Figure 16:
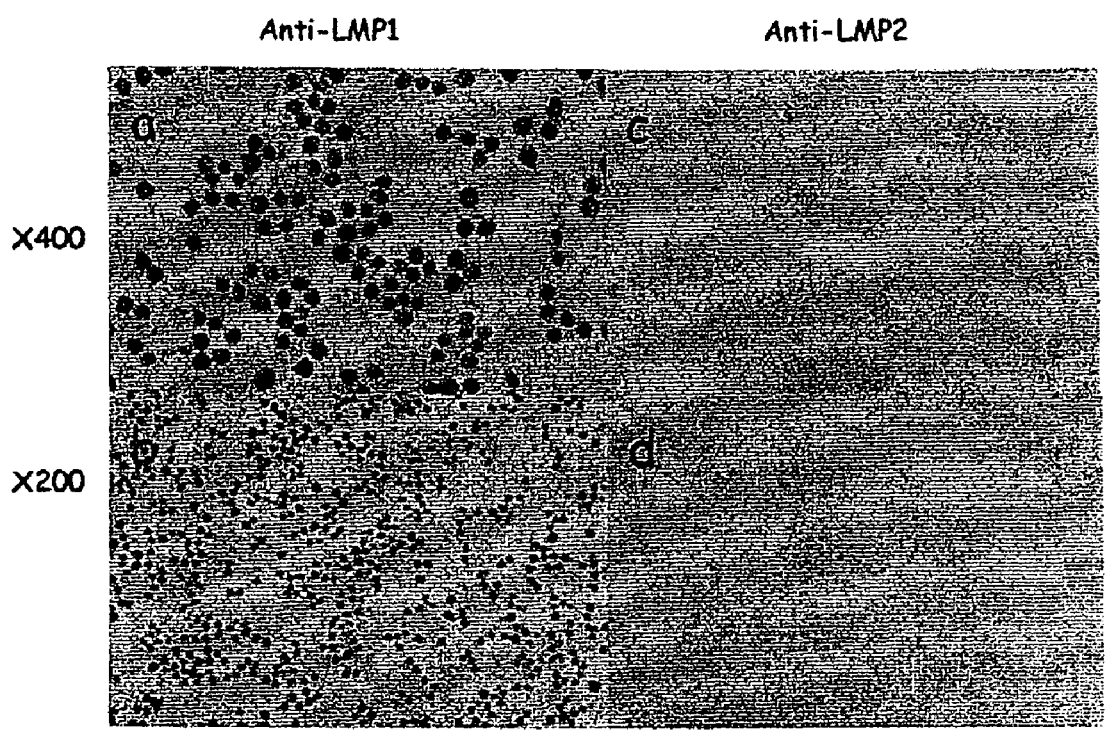
FIG. 16 illustrates the detection, by immunocytochemistry using the immune serum specific for the extracellular domains of LMP1, of the native LMP1 protein present at the surface of the Sp2o line stably transfected with the vector pREP4-LMP1. The anti-LMP2A antibody is used as a control. The cells are fixed in PBS buffer containing 4% formaldehyde and the labeling with the antibodies is visualized as described in examples 1.7, 4 and 8. a and b: labeling with the anti-LMP1 antibody produced as described in example 2, respectively at magnification×400 and ×200. c and d: labeling with the anti-LMP2A antibody produced as described in example 8, respectively at magnification ×400 and ×200.

The Sp2o cell line, which has a BALB/c genetic background, makes it possible to obtain tumors in BALB/c mice. A stable line expressing LMP1 was selected from semi-adherent Sp2o cells transfected with the recombinant vector pREP4-LMP1, and then the expression of LMP1 in the transfected line was analyzed, as described in example 8. After four weeks of growth in the selected medium, all the cells are evenly labeled with the antibody against LMP1 extracellular loops (FIGS. 16a and 16b). No labeling of the Sp2o-LMP1 line is obtained with the antibodies directed against the LMP2 extracellular loops (FIGS. 16c and 16d) or alternatively with normal serum.

b) Preventive Immunization

Forty one BALB/c mice (7 weeks old) are immunized according to a standard protocol described above in example 1. The mice are given an injection, either of KLH (n=21), or of the peptide that mimics the LMP1 extracellular loops (SEQ ID NO. 10) coupled to KLH (n=20). Five days before the injection of Sp2o-pREP-4-LMP1 cells, the mice of each batch are given a booster injection, respectively with KLH or KLH coupled to the peptide SEQ ID No. 10.

The mice of the control group (KLH: n=21) are given an interscapular subcutaneous injection of 1 million Sp2o-pREP4-LMP1 cells. The mice immunized against the peptide that mimics the LMP1 extracellular loops are separated into two batches of 10 mice, and each is given, on the same day and from the same preparation of Sp2o-pREP4-LMP1 cells, an interscapular subcutaneous injection of 1 or 3 million cells in a volume of 100 µl of 0.9% NaCl.

Figure 17:
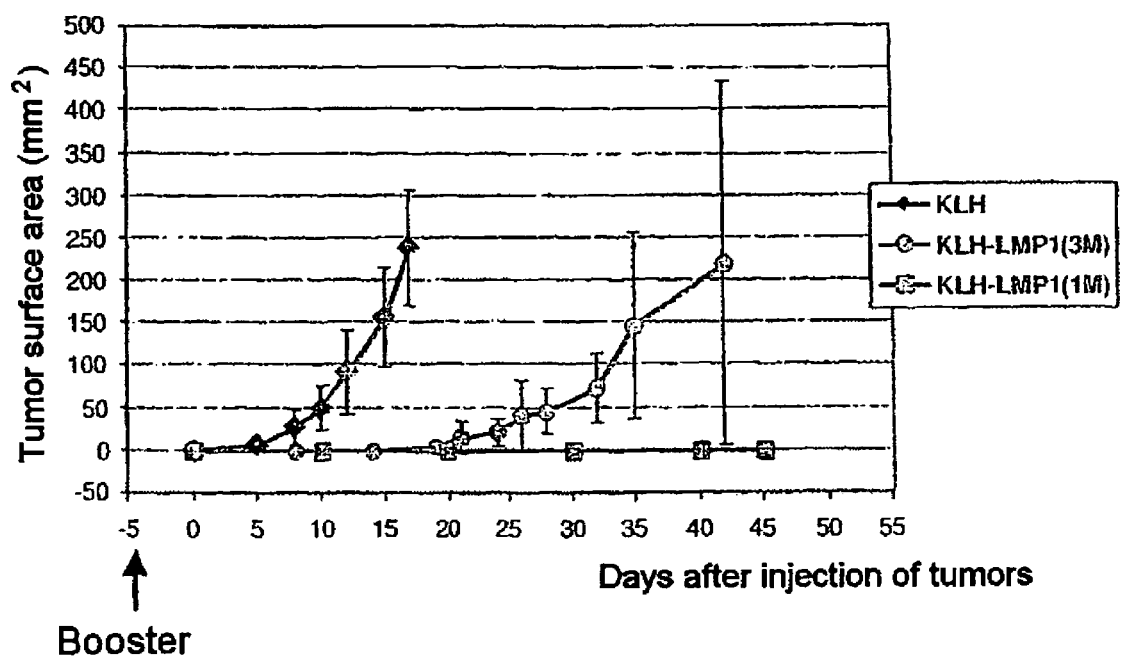
FIG. 17 illustrates the inhibition of tumors expressing LMP1 (Sp2o-pREP4LMP1 line) in the mice immunized with the peptide antigen that mimics the extracellular domains (ED1+ED2; SEQ ID No. 10) of LMP1, by comparison with the control mice given an injection of KLH. The mice of the control group (KLH: n=21) and a first group (n=10) of mice immunized with the LMP1 antigen were given a subcutaneous injection of one million Sp2o-pREP4-LMP1 cells. A second group of mice immunized with the LMP1 antigen (n=10) was given a subcutaneous injection of three million Sp2o-pREP4-LMP1 cells.

FIG. 17 shows that the Sp2o cells transfected with pREP4-LMP1 are particularly aggressive and produce very rapidly growing tumors. The tumors develop in most of the control mice (KLH) from the first week (D+5) following injection. By 15 days, all the mice had to be sacrificed since the tumors exceeded a threshold surface area of 250 mm$^2$.

On the other hand, none of the mice given 1 million Sp2o-pREP4-LMP1 cells (KLH-LMP1 (1 M), FIG. 17) developed a tumor more than 45 days following the inoculation. When the amount of cells injected is taken to 3 millions per mouse (KLH-LMP1 (3 M), FIG. 17), palpable tumors emerge after 23 days in certain mice. The considerable standard deviations for this curve take into account the large individual variation in the size of the tumors encountered in this treated group (KLH-LMP1 (3 M), FIG. 17). However, the progression of the tumors is slow in this group and two of the 10 treated mice remained free of any tumor.

In conclusion, all these results show that it is possible to obtain a very good humoral response against type III membrane proteins of parasitic, viral or bacterial origins as defined in FIG. 2, and to treat and immunize patients against infection with these microorganisms, by mimicking, with peptide constructs, the structure of the extracellular loops of these membrane proteins that are naturally relatively nonimmunogenic.

As emerges from the above, the invention is in no way limited to its methods of implementation, execution and application which have just been described more explicitly; on the contrary, it encompasses all the variants thereof which may occur to those skilled in the art, without departing from the context or the scope of the present invention.

The invention claimed is:

1. A chimeric antigen derived from Epstein-Barr virus (EBV), comprising an amino acid sequence selected from the group consisting of the sequences set forth in SEQ ID NO: 10, 11 and 13 to 23.

2. An immunogenic composition comprising an antigen combined with at least one pharmaceutically acceptable vehicle, wherein the antigen comprises an amino acid sequence selected from the group consisting of the sequences set forth in SEQ ID NO: 10, 11 and 13 to 23.

* * * * *

SEQUENCE LISTING

<160> NUMBER OF SEQ ID NOS: 34

<210> SEQ ID NO 1
<211> LENGTH: 7
<212> TYPE: PRT
<213> ORGANISM: Epstein Barr Virus

<400> SEQUENCE: 1

Ser Asp Trp Thr Gly Gly Ala
1               5

<210> SEQ ID NO 2
<211> LENGTH: 7
<212> TYPE: PRT
<213> ORGANISM: Epstein Barr Virus

<400> SEQUENCE: 2

Trp Asn Leu His Gly Gln Ala

```
                                   1               5

<210> SEQ ID NO 3
<211> LENGTH: 6
<212> TYPE: PRT
<213> ORGANISM: Epstein Barr Virus

<400> SEQUENCE: 3

Leu Gln Gln Asn Trp Asn
 1               5

<210> SEQ ID NO 4
<211> LENGTH: 8
<212> TYPE: PRT
<213> ORGANISM: Epstein Barr Virus

<400> SEQUENCE: 4

Ser Cys Phe Thr Ala Ser Val Ser
 1               5

<210> SEQ ID NO 5
<211> LENGTH: 9
<212> TYPE: PRT
<213> ORGANISM: Epstein Barr Virus

<400> SEQUENCE: 5

Arg Ile Glu Asp Pro Pro Phe Asn Ser
 1               5

<210> SEQ ID NO 6
<211> LENGTH: 7
<212> TYPE: PRT
<213> ORGANISM: Epstein Barr Virus

<400> SEQUENCE: 6

Asp Ala Val Leu Gln Leu Ser
 1               5

<210> SEQ ID NO 7
<211> LENGTH: 4
<212> TYPE: PRT
<213> ORGANISM: Epstein Barr Virus

<400> SEQUENCE: 7

Gly Thr Leu Asn
 1

<210> SEQ ID NO 8
<211> LENGTH: 18
<212> TYPE: PRT
<213> ORGANISM: Epstein Barr Virus

<400> SEQUENCE: 8

Ser Ile Leu Gln Thr Asn Phe Lys Ser Leu Ser Ser Thr Glu Phe Ile
 1               5                  10                  15

Pro Asn

<210> SEQ ID NO 9
<211> LENGTH: 6
<212> TYPE: PRT
<213> ORGANISM: Epstein Barr Virus

<400> SEQUENCE: 9

Ser Asn Thr Leu Leu Ser
```

```
<210> SEQ ID NO 10
<211> LENGTH: 19
<212> TYPE: PRT
<213> ORGANISM: Epstein Barr Virus

<400> SEQUENCE: 10

Met Ser Asp Trp Thr Gly Gly Ala Leu Cys Leu Trp Asn Leu His Gly
 1               5                  10                  15

Gln Ala Leu

<210> SEQ ID NO 11
<211> LENGTH: 19
<212> TYPE: PRT
<213> ORGANISM: Epstein Barr Virus

<400> SEQUENCE: 11

Leu Trp Asn Leu His Gly Gln Ala Leu Cys Leu Tyr Leu Gln Gln Asn
 1               5                  10                  15

Trp Trp Thr

<210> SEQ ID NO 12
<211> LENGTH: 19
<212> TYPE: PRT
<213> ORGANISM: Epstein Barr Virus

<400> SEQUENCE: 12

Met Ser Asp Trp Thr Gly Gly Ala Leu Cys Leu Tyr Leu Gln Gln Asn
 1               5                  10                  15

Trp Trp Thr

<210> SEQ ID NO 13
<211> LENGTH: 30
<212> TYPE: PRT
<213> ORGANISM: Epstein Barr Virus

<400> SEQUENCE: 13

Cys Met Ser Asp Trp Thr Gly Gly Ala Leu Cys Leu Trp Asn Leu His
 1               5                  10                  15

Gly Gln Ala Leu Cys Tyr Leu Gln Gln Asn Trp Trp Thr Cys
             20                  25                  30

<210> SEQ ID NO 14
<211> LENGTH: 29
<212> TYPE: PRT
<213> ORGANISM: Epstein Barr Virus

<400> SEQUENCE: 14

Met Ser Asp Trp Thr Gly Gly Ala Leu Cys Leu Trp Asn Leu His Gly
 1               5                  10                  15

Gln Ala Leu Cys Leu Tyr Leu Gln Gln Asn Trp Trp Thr
             20                  25

<210> SEQ ID NO 15
<211> LENGTH: 23
<212> TYPE: PRT
<213> ORGANISM: Epstein Barr Virus

<400> SEQUENCE: 15

Ala Ser Ser Phe Thr Ala Ser Val Ser Thr Cys Thr Trp Arg Ile Glu
 1               5                  10                  15
```

```
Asp Pro Pro Phe Asn Ser Leu
            20

<210> SEQ ID NO 16
<211> LENGTH: 23
<212> TYPE: PRT
<213> ORGANISM: Epstein Barr Virus

<400> SEQUENCE: 16

Thr Trp Arg Ile Glu Asp Pro Pro Phe Asn Ser Leu Cys Val Asp Ala
1               5                   10                  15

Val Leu Gln Leu Ser Pro Leu
            20

<210> SEQ ID NO 17
<211> LENGTH: 22
<212> TYPE: PRT
<213> ORGANISM: Epstein Barr Virus

<400> SEQUENCE: 17

Ile Val Asp Ala Val Leu Gln Leu Ser Pro Leu Cys Ile Leu Gly Thr
1               5                   10                  15

Leu Asn Leu Thr Thr Met
            20

<210> SEQ ID NO 18
<211> LENGTH: 32
<212> TYPE: PRT
<213> ORGANISM: Epstein Barr Virus

<400> SEQUENCE: 18

Ile Leu Gly Thr Leu Asn Leu Thr Thr Met Cys Gly Gly Ser Ile Leu
1               5                   10                  15

Gln Thr Asn Phe Lys Ser Leu Ser Ser Thr Glu Phe Ile Pro Asn Leu
            20                  25                  30

<210> SEQ ID NO 19
<211> LENGTH: 32
<212> TYPE: PRT
<213> ORGANISM: Epstein Barr Virus

<400> SEQUENCE: 19

Gly Gly Ser Ile Leu Gln Thr Asn Phe Lys Ser Leu Ser Ser Thr Glu
1               5                   10                  15

Phe Ile Pro Asn Leu Cys Val Met Ser Asn Thr Leu Leu Ser Ala Trp
            20                  25                  30

<210> SEQ ID NO 20
<211> LENGTH: 34
<212> TYPE: PRT
<213> ORGANISM: Epstein Barr Virus

<400> SEQUENCE: 20

Ala Ser Ser Phe Thr Ala Ser Val Ser Thr Cys Thr Trp Arg Ile Glu
1               5                   10                  15

Asp Pro Pro Phe Asn Ser Leu Cys Val Asp Ala Val Leu Gln Leu Ser
            20                  25                  30

Pro Leu

<210> SEQ ID NO 21
<211> LENGTH: 34
```

```
<212> TYPE: PRT
<213> ORGANISM: Epstein Barr Virus

<400> SEQUENCE: 21

Thr Trp Arg Ile Glu Asp Pro Pro Phe Asn Ser Leu Cys Val Asp Ala
1               5                   10                  15

Val Leu Gln Leu Ser Pro Leu Cys Ile Leu Gly Thr Leu Asn Leu Thr
                20                  25                  30

Thr Met

<210> SEQ ID NO 22
<211> LENGTH: 41
<212> TYPE: PRT
<213> ORGANISM: Epstein Barr Virus

<400> SEQUENCE: 22

Val Asp Ala Val Leu Gln Leu Ser Pro Leu Cys Ile Leu Gly Thr Leu
1               5                   10                  15

Asn Leu Thr Cys Gly Gly Ser Ile Leu Gln Thr Asn Phe Lys Ser Leu
                20                  25                  30

Ser Ser Thr Glu Phe Ile Pro Asn Leu
            35                  40

<210> SEQ ID NO 23
<211> LENGTH: 64
<212> TYPE: PRT
<213> ORGANISM: Epstein Barr Virus

<400> SEQUENCE: 23

Ile Leu Gly Thr Leu Asn Leu Thr Cys Gly Gly Ser Ile Leu Gln Thr
1               5                   10                  15

Asn Phe Lys Ser Leu Ser Ser Thr Glu Phe Ile Pro Asn Leu Cys Val
                20                  25                  30

Met Ser Asn Thr Leu Leu Ser Ala Trp Thr Trp Arg Ile Glu Asp Pro
            35                  40                  45

Pro Phe Asn Ser Leu Cys Val Asp Ala Val Leu Gln Leu Ser Pro Leu
        50                  55                  60

<210> SEQ ID NO 24
<211> LENGTH: 6
<212> TYPE: PRT
<213> ORGANISM: Epstein Barr Virus

<400> SEQUENCE: 24

Val Met Ser Asp Trp Thr
1               5

<210> SEQ ID NO 25
<211> LENGTH: 6
<212> TYPE: PRT
<213> ORGANISM: Epstein Barr Virus

<400> SEQUENCE: 25

Asn Leu His Gly Gln Ala
1               5

<210> SEQ ID NO 26
<211> LENGTH: 4
<212> TYPE: PRT
<213> ORGANISM: Epstein Barr Virus

<400> SEQUENCE: 26
```

Leu Gln Gln Asn
 1

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
agaattcatg gggtccctag aa                                              22

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
aggtacctta tagagtgttg cga                                             23

<210> SEQ ID NO 29
<211> LENGTH: 386
<212> TYPE: PRT
<213> ORGANISM: Human herpesvirus 4

<400> SEQUENCE: 29

Met Glu His Asp Leu Glu Arg Gly Pro Pro Gly Pro Arg Arg Pro Pro
 1               5                  10                  15

Arg Gly Pro Pro Leu Ser Ser Ser Leu Gly Leu Ala Leu Leu Leu Leu
                20                  25                  30

Leu Leu Ala Leu Leu Phe Trp Leu Tyr Ile Val Met Ser Asp Trp Thr
            35                  40                  45

Gly Gly Ala Leu Leu Val Leu Tyr Ser Phe Ala Leu Met Leu Ile Ile
        50                  55                  60

Ile Ile Leu Ile Ile Phe Ile Phe Arg Arg Asp Leu Leu Cys Pro Leu
65                  70                  75                  80

Gly Ala Leu Cys Ile Leu Leu Leu Met Ile Thr Leu Leu Leu Ile Ala
                85                  90                  95

Leu Trp Asn Leu His Gly Gln Ala Leu Phe Leu Gly Ile Val Leu Phe
            100                 105                 110

Ile Phe Gly Cys Leu Leu Val Leu Gly Ile Trp Ile Tyr Leu Leu Glu
        115                 120                 125

Met Leu Trp Arg Leu Gly Ala Thr Ile Trp Gln Leu Leu Ala Phe Phe
    130                 135                 140

Leu Ala Phe Phe Leu Asp Leu Ile Leu Leu Ile Ile Ala Leu Tyr Leu
145                 150                 155                 160

Gln Gln Asn Trp Trp Thr Leu Leu Val Asp Leu Leu Trp Leu Leu Leu
                165                 170                 175

Phe Leu Ala Ile Leu Ile Trp Met Tyr Tyr His Gly Gln Arg His Ser
            180                 185                 190

Asp Glu His His His Asp Asp Ser Leu Pro His Pro Gln Gln Ala Thr
        195                 200                 205

Asp Asp Ser Gly His Glu Ser Asp Ser Asn Ser Asn Glu Gly Arg His
    210                 215                 220

His Leu Leu Val Ser Gly Ala Gly Asp Gly Pro Pro Leu Cys Ser Gln

```
                225                 230                 235                 240
Asn Leu Gly Ala Pro Gly Gly Gly Pro Asp Asn Gly Pro Gln Asp Pro
                245                 250                 255

Asp Asn Thr Asp Asp Asn Gly Pro Gln Asp Pro Asp Asn Thr Asp Asp
            260                 265                 270

Asn Gly Pro His Asp Pro Leu Pro Gln Asp Pro Asp Asn Thr Asp Asp
            275                 280                 285

Asn Gly Pro Gln Asp Pro Asp Asn Thr Asp Asp Asn Gly Pro His Asp
        290                 295                 300

Pro Leu Pro His Ser Pro Ser Asp Ser Ala Gly Asn Asp Gly Pro
305                 310                 315                 320

Pro Gln Leu Thr Glu Glu Val Glu Asn Lys Gly Gly Asp Gln Gly Pro
                325                 330                 335

Pro Leu Met Thr Asp Gly Gly Gly His Ser His Asp Ser Gly His
                340                 345                 350

Gly Gly Gly Asp Pro His Leu Pro Thr Leu Leu Gly Ser Ser Gly
            355                 360                 365

Ser Gly Gly Asp Asp Asp Pro His Gly Pro Val Gln Leu Ser Tyr
        370                 375                 380

Tyr Asp
385

<210> SEQ ID NO 30
<211> LENGTH: 497
<212> TYPE: PRT
<213> ORGANISM: Human herpesvirus 4

<400> SEQUENCE: 30

Met Gly Ser Leu Glu Met Val Pro Met Gly Ala Gly Pro Pro Ser Pro
1               5                   10                  15

Gly Gly Asp Pro Asp Gly Tyr Asp Gly Gly Asn Asn Ser Gln Tyr Pro
            20                  25                  30

Ser Ala Ser Gly Ser Ser Gly Asn Thr Pro Thr Pro Pro Asn Asp Glu
        35                  40                  45

Glu Arg Glu Ser Asn Glu Glu Pro Pro Pro Tyr Glu Asp Pro Tyr
    50                  55                  60

Trp Gly Asn Gly Asp Arg His Ser Asp Tyr Gln Pro Leu Gly Thr Gln
65                  70                  75                  80

Asp Gln Ser Leu Tyr Leu Gly Leu Gln His Asp Gly Asn Asp Gly Leu
                85                  90                  95

Pro Pro Pro Pro Tyr Ser Pro Arg Asp Asp Ser Ser Gln His Ile Tyr
            100                 105                 110

Glu Glu Ala Gly Arg Gly Ser Met Asn Pro Val Cys Leu Pro Val Ile
        115                 120                 125

Val Ala Pro Tyr Leu Phe Trp Leu Ala Ala Ile Ala Ala Ser Cys Phe
    130                 135                 140

Thr Ala Ser Val Ser Thr Val Val Thr Ala Thr Gly Leu Ala Leu Ser
145                 150                 155                 160

Leu Leu Leu Leu Ala Ala Val Ala Ser Ser Tyr Ala Ala Ala Gln Arg
                165                 170                 175

Lys Leu Leu Thr Pro Val Thr Val Leu Thr Ala Val Val Thr Phe Phe
            180                 185                 190

Ala Ile Cys Leu Thr Trp Arg Ile Glu Asp Pro Pro Phe Asn Ser Leu
        195                 200                 205
```

```
Leu Phe Ala Leu Leu Ala Ala Gly Gly Leu Gln Gly Ile Tyr Val
    210                 215                 220
Leu Val Met Leu Val Leu Ile Leu Ala Tyr Arg Arg Arg Trp Arg
225                 230                 235                 240
Arg Leu Thr Val Cys Gly Gly Ile Met Phe Leu Ala Cys Val Leu Val
                245                 250                 255
Leu Ile Val Asp Ala Val Leu Gln Leu Ser Pro Leu Leu Gly Ala Val
            260                 265                 270
Thr Val Val Ser Met Thr Leu Leu Leu Ala Phe Val Leu Trp Leu
        275                 280                 285
Ser Ser Pro Gly Gly Leu Gly Thr Leu Gly Ala Ala Leu Leu Thr Leu
    290                 295                 300
Ala Ala Ala Leu Ala Leu Leu Ala Ser Leu Ile Leu Gly Thr Leu Asn
305                 310                 315                 320
Leu Thr Thr Met Phe Leu Leu Met Leu Leu Trp Thr Leu Val Val Leu
                325                 330                 335
Leu Ile Cys Ser Ser Cys Ser Ser Cys Pro Leu Ser Lys Ile Leu Leu
            340                 345                 350
Ala Arg Leu Phe Leu Tyr Ala Leu Ala Leu Leu Leu Ala Ser Ala
        355                 360                 365
Leu Ile Ala Gly Gly Ser Ile Leu Gln Thr Asn Phe Lys Ser Leu Ser
    370                 375                 380
Ser Thr Glu Phe Ile Pro Asn Leu Phe Cys Met Leu Leu Ile Val
385                 390                 395                 400
Ala Gly Ile Leu Phe Ile Leu Ala Ile Leu Thr Glu Trp Gly Ser Gly
                405                 410                 415
Asn Arg Thr Tyr Gly Pro Val Phe Met Cys Leu Gly Gly Leu Leu Thr
            420                 425                 430
Met Val Ala Gly Ala Val Trp Leu Thr Val Met Ser Asn Thr Leu Leu
        435                 440                 445
Ser Ala Trp Ile Leu Thr Ala Gly Phe Leu Ile Phe Leu Ile Gly Phe
    450                 455                 460
Ala Leu Phe Gly Val Ile Arg Cys Cys Arg Tyr Cys Cys Tyr Tyr Cys
465                 470                 475                 480
Leu Thr Leu Glu Ser Glu Glu Arg Pro Pro Thr Pro Tyr Arg Asn Thr
                485                 490                 495
Val

<210> SEQ ID NO 31
<211> LENGTH: 489
<212> TYPE: PRT
<213> ORGANISM: Human herpesvirus 8

<400> SEQUENCE: 31

Met Lys Thr Leu Ile Phe Phe Trp Asn Leu Trp Leu Trp Ala Leu Leu
  1               5                  10                  15
Val Cys Phe Trp Cys Ile Thr Leu Val Cys Val Thr Thr Asn Ser Ile
                20                  25                  30
Asp Thr Met Ala Ser Leu Leu Val Met Cys Ile Leu Phe Val Ser Ala
            35                  40                  45
Ile Asn Lys Tyr Thr Gln Ala Ile Ser Ser Asn Asn Pro Lys Trp Pro
        50                  55                  60
Ser Ser Trp His Leu Gly Ile Ile Ala Cys Ile Val Leu Lys Leu Trp
65                  70                  75                  80
```

-continued

```
Asn Leu Ser Thr Thr Asn Ser Val Thr Tyr Ala Cys Leu Ile Thr Thr
                85                  90                  95
Ala Ile Leu Ser Leu Val Thr Ala Phe Leu Thr Leu Ile Lys His Cys
            100                 105                 110
Thr Ala Cys Lys Leu Gln Leu Glu His Gly Ile Leu Phe Thr Ser Thr
        115                 120                 125
Phe Ala Val Leu Met Thr Asn Met Leu Val His Met Ser Asn Thr Trp
    130                 135                 140
Gln Ser Ser Trp Ile Phe Phe Pro Ile Ser Phe Thr Leu Ser Leu Pro
145                 150                 155                 160
Phe Leu Tyr Ala Phe Ala Thr Val Lys Thr Gly Asn Ile Lys Leu Val
                165                 170                 175
Ser Ser Val Ser Phe Ile Cys Ala Gly Leu Val Met Gly Tyr Pro Val
            180                 185                 190
Ser Cys Cys Lys Thr His Thr Cys Thr Ala Thr Ala Ala Gly Leu Ser
        195                 200                 205
Leu Ser Ser Ile Tyr Leu Gly Phe Thr Gly Ile Ile Ser Thr Leu His
    210                 215                 220
Lys Ser Trp Ala Pro Lys Arg Gly Ile Leu Thr Phe Leu Leu Leu
225                 230                 235                 240
Gln Gly Gly Val Leu Thr Thr Gln Thr Leu Thr Thr Glu Leu Leu Ala
                245                 250                 255
Ile Thr Ser Thr Thr Gly Asn Ile Lys Gly His Glu Ile Leu Leu Leu
            260                 265                 270
Val Cys Leu Ile Phe Leu Trp Cys Leu Tyr Val Trp Gln Ser Phe Asn
        275                 280                 285
Lys Ala Ser Leu Val Thr Gly Met Leu His Leu Ile Ala Ala Trp Ser
    290                 295                 300
His Thr Gly Gly Cys Val Gln Leu Val Met Leu Leu Pro Ser Gly Leu
305                 310                 315                 320
Thr Arg Gly Ile Leu Thr Met Ile Ile Cys Ile Ser Thr Leu Phe Ser
                325                 330                 335
Thr Leu Gln Gly Leu Leu Val Phe Tyr Leu Tyr Lys Glu Lys Lys Val
            340                 345                 350
Val Ala Val Asn Ser Tyr Arg Gln Arg Arg Arg Ile Tyr Thr Arg
        355                 360                 365
Asp Gln Asn Leu His His Asn Asp Asn His Leu Gly Asn Asn Val Ile
    370                 375                 380
Ser Pro Pro Leu Pro Phe Arg Gln Pro Val Arg Leu Pro
385                 390                 395                 400
Ser His Val Thr Asp Arg Gly Arg Gly Ser Gln Pro Leu Asn Glu Val
                405                 410                 415
Glu Leu Gln Glu Val Asn Arg Asp Pro Pro Asn Val Phe Gly Tyr Ala
            420                 425                 430
Ser Ile Leu Val Ser Gly Ala Glu Glu Ser Arg Glu Pro Ser Pro Gln
        435                 440                 445
Pro Asp Gln Ser Gly Met Ser Ile Leu Arg Val Asp Gly Gly Ser Ala
    450                 455                 460
Phe Arg Ile Asp Thr Ala Gln Ala Ala Thr Gln Pro Thr Asp Asp Leu
465                 470                 475                 480
Tyr Glu Glu Val Leu Phe Pro Arg Asn
                485
```

<210> SEQ ID NO 32
<211> LENGTH: 498
<212> TYPE: PRT
<213> ORGANISM: Human herpesvirus 8

<400> SEQUENCE: 32

Met Asn Tyr Lys Lys Tyr Leu Trp Gly Thr Trp Phe Ala Ala Leu Ile
1               5                   10                  15

Thr Cys Cys Gly Cys Leu Ser Ile Met Phe Cys Leu Leu Thr Ile Asn
            20                  25                  30

Leu Gln Asn Thr Ile Phe Leu Leu Ser Asn Ile Ser Val Tyr Tyr Gln
        35                  40                  45

Leu Phe Cys Thr Ile Thr Asn Ile Tyr Val Gln Ser Lys Lys Gln Arg
    50                  55                  60

Phe Gln Ala Ser Pro Pro Ile Gly Pro Ser Ile Val Gly Cys Ile
65                  70                  75                  80

Ala Phe Ala Ser Trp Ser Phe Ser Thr Gln Ser Thr Leu Ser Thr Val
                85                  90                  95

Cys Val Cys Ile Ile Ser Leu Leu Ser Ile Ile Thr Ala Ile Leu Ser
            100                 105                 110

Leu Gly Gly Thr Leu Arg Val Val Lys Cys Thr Ile Asp Ser Gly Leu
        115                 120                 125

Leu Cys Ile Val Met Val Leu Val Leu Ile Phe Ser Met Gly Leu Gln
    130                 135                 140

Ile Tyr Asn Asn Trp Thr His Cys Gln Phe Phe Leu Pro Leu Trp Thr
145                 150                 155                 160

Leu Leu Leu Val Phe Phe Ile His Ile Phe Ala Thr Asp Asn Gly Pro
                165                 170                 175

Cys Leu Lys Leu Ala Ala Cys Val Phe Ala Ile Cys Gly Gly Ile Leu
            180                 185                 190

Lys Ala Thr Pro Ala Phe Phe Cys Val Ser His Ser Cys Leu Ser Val
        195                 200                 205

Ile Ile Ala Gly Cys Ile Ser Cys Ile His Ile Gly Met Thr Gly Leu
    210                 215                 220

Phe Ile Thr Met Lys Arg His Trp Ile Gly Ser Thr Lys Gly Leu Met
225                 230                 235                 240

Ser Phe Leu Leu Leu Gln Gly Gly Val Leu Val Thr Leu Thr Thr Thr
                245                 250                 255

Ile Gly Ile Leu Phe Ile Lys Arg Glu Gln Asp Thr Asn Asn Glu Gly
            260                 265                 270

Ser Ile Thr Leu Leu Ala Gly Cys Gly Phe Leu Leu Tyr Cys Phe Phe
        275                 280                 285

Cys Trp Gln Ser Phe His Lys Ala Ser Leu Ser Gly Gly Phe Leu Phe
    290                 295                 300

Leu Phe Leu Ala Trp Thr Cys Ala Gly Cys Cys Val Lys Leu Val Leu
305                 310                 315                 320

Leu Tyr Thr Asp Gly Trp Thr Thr Gly Val Thr Ser Gly Leu Ile Cys
                325                 330                 335

Val Ile Val Ile Leu Ser Thr Gly Gln Ala Val Leu Val Gly Tyr Leu
            340                 345                 350

Tyr Arg Glu Ser Arg Leu Val Ser Phe Asn Asn Val Thr Thr Arg Leu
        355                 360                 365

Pro Ile Tyr Thr Pro His Asp Thr Pro His Ala His Ala Gly Arg Ile
    370                 375                 380

```
Cys Pro Asp Val Asn His Leu Ala Arg Arg Leu Pro Pro Leu Pro Ser
385                 390                 395                 400

Arg Asn Val Ile His Ser Arg Ile Leu Ser Ser Thr Thr Asp Met Ala
            405                 410                 415

Leu Ser Pro Val Arg Val Cys Asn Thr Glu Val Thr Thr Gln Leu Glu
        420                 425                 430

Met Gln Gln Leu His Ser Glu Arg Thr Val Thr Tyr Ala Ser Ile Leu
    435                 440                 445

Gly Asp Asn Thr Pro Pro Thr Arg Ala Ser Ala Cys Ile Asn Gln
450                 455                 460

Ser Gly Ile Ser Asn Val Ser Asn Cys Gly Val Arg Ser Leu Asp Pro
465                 470                 475                 480

Pro Pro Phe Gln Pro Ala Asp Glu Val Tyr Glu Glu Val Leu Phe Pro
            485                 490                 495

Thr Asp

<210> SEQ ID NO 33
<211> LENGTH: 3011
<212> TYPE: PRT
<213> ORGANISM: Hepatitis C virus

<400> SEQUENCE: 33

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Ser Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Val Thr Pro Thr Val Ala Thr Arg Asp Gly Lys Leu Pro Thr Thr
                245                 250                 255
```

-continued

```
Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Asp Cys
    290                 295                 300

Asn Cys Ser Ile Tyr Pro Gly His Ile Thr Gly His Arg Met Ala Trp
305                 310                 315                 320

Asp Met Met Met Asn Trp Ser Pro Thr Ala Ala Leu Val Val Ala Gln
                325                 330                 335

Leu Leu Arg Ile Pro Gln Ala Ile Met Asp Met Ile Ala Gly Ala His
            340                 345                 350

Trp Gly Val Leu Ala Gly Ile Ala Tyr Phe Ser Met Val Gly Asn Trp
        355                 360                 365

Ala Lys Val Leu Val Val Leu Leu Leu Phe Ala Gly Val Asp Ala Glu
    370                 375                 380

Thr His Val Thr Gly Gly Ser Ala Gly Arg Thr Thr Ala Gly Leu Val
385                 390                 395                 400

Gly Leu Leu Thr Pro Gly Ala Lys Gln Asn Ile Gln Leu Ile Asn Thr
                405                 410                 415

Asn Gly Ser Trp His Ile Asn Ser Thr Ala Leu Asn Cys Asn Glu Ser
            420                 425                 430

Leu Asn Thr Gly Trp Leu Ala Gly Leu Phe Tyr Gln His Lys Phe Asn
        435                 440                 445

Ser Ser Gly Cys Pro Glu Arg Leu Ala Ser Cys Arg Arg Leu Thr Asp
    450                 455                 460

Phe Ala Gln Gly Trp Gly Pro Ile Ser Tyr Ala Asn Gly Ser Gly Leu
465                 470                 475                 480

Asp Glu Arg Pro Tyr Cys Trp His Tyr Pro Pro Arg Pro Cys Gly Ile
                485                 490                 495

Val Pro Ala Lys Ser Val Cys Gly Pro Val Tyr Cys Phe Thr Pro Ser
            500                 505                 510

Pro Val Val Gly Thr Thr Asp Arg Ser Gly Ala Pro Thr Tyr Ser
        515                 520                 525

Trp Gly Ala Asn Asp Thr Asp Val Phe Val Leu Asn Asn Thr Arg Pro
    530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Val Gly Asn
                565                 570                 575

Asn Thr Leu Leu Cys Pro Thr Asp Cys Phe Arg Lys His Pro Glu Ala
            580                 585                 590

Thr Tyr Ser Arg Cys Gly Ser Gly Pro Trp Ile Thr Pro Arg Cys Met
        595                 600                 605

Val Asp Tyr Pro Tyr Arg Leu Trp His Tyr Pro Cys Thr Ile Asn Tyr
    610                 615                 620

Thr Ile Phe Lys Val Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
                645                 650                 655

Arg Asp Arg Ser Glu Leu Ser Pro Leu Leu Leu Ser Thr Thr Gln Trp
            660                 665                 670

Gln Val Leu Pro Cys Ser Phe Thr Thr Leu Pro Ala Leu Ser Thr Gly
```

```
                    675                 680                 685
Leu Ile His Leu His Gln Asn Ile Val Asp Val Gln Tyr Leu Tyr Gly
            690                 695                 700
Val Gly Ser Ser Ile Ala Ser Trp Ala Ile Lys Trp Glu Tyr Val Val
705                 710                 715                 720
Leu Leu Phe Leu Leu Leu Ala Asp Ala Arg Val Cys Ser Cys Leu Trp
                725                 730                 735
Met Met Leu Leu Ile Ser Gln Ala Glu Ala Ala Leu Glu Asn Leu Val
                    740                 745                 750
Ile Leu Asn Ala Ala Ser Leu Ala Gly Thr His Gly Leu Val Ser Phe
            755                 760                 765
Leu Val Phe Phe Cys Phe Ala Trp Tyr Leu Lys Gly Arg Trp Val Pro
            770                 775                 780
Gly Ala Val Tyr Ala Phe Tyr Gly Met Trp Pro Leu Leu Leu Leu Leu
785                 790                 795                 800
Leu Ala Leu Pro Gln Arg Ala Tyr Ala Leu Asp Thr Glu Val Ala Ala
                805                 810                 815
Ser Cys Gly Gly Val Val Leu Val Gly Leu Met Ala Leu Thr Leu Ser
            820                 825                 830
Pro Tyr Tyr Lys Arg Tyr Ile Ser Trp Cys Met Trp Trp Leu Gln Tyr
            835                 840                 845
Phe Leu Thr Arg Val Glu Ala Gln Leu His Val Trp Val Pro Pro Leu
        850                 855                 860
Asn Val Arg Gly Gly Arg Asp Ala Val Ile Leu Leu Met Cys Val Val
865                 870                 875                 880
His Pro Thr Leu Val Phe Asp Ile Thr Lys Leu Leu Leu Ala Ile Phe
                885                 890                 895
Gly Pro Leu Trp Ile Leu Gln Ala Ser Leu Leu Lys Val Pro Tyr Phe
                900                 905                 910
Val Arg Val Gln Gly Leu Leu Arg Ile Cys Ala Leu Ala Arg Lys Ile
                915                 920                 925
Ala Gly Gly His Tyr Val Gln Met Ala Ile Ile Lys Leu Gly Ala Leu
            930                 935                 940
Thr Gly Thr Tyr Val Tyr Asn His Leu Thr Pro Leu Arg Asp Trp Ala
945                 950                 955                 960
His Asn Gly Leu Arg Asp Leu Ala Val Ala Val Glu Pro Val Val Phe
                965                 970                 975
Ser Arg Met Glu Thr Lys Leu Ile Thr Trp Gly Ala Asp Thr Ala Ala
                980                 985                 990
Cys Gly Asp Ile Ile Asn Gly Leu Pro Val Ser Ala Arg Arg Gly Gln
            995                 1000                1005
Glu Ile Leu Leu Gly Pro Ala Asp Gly Met Val Ser Lys Gly Trp Arg
    1010                1015                1020
Leu Leu Ala Pro Ile Thr Ala Tyr Ala Gln Gln Thr Arg Gly Leu Leu
1025                1030                1035                1040
Gly Cys Ile Ile Thr Ser Leu Thr Gly Arg Asp Lys Asn Gln Val Glu
                1045                1050                1055
Gly Glu Val Gln Ile Val Ser Thr Ala Thr Gln Thr Phe Leu Ala Thr
                1060                1065                1070
Cys Ile Asn Gly Val Cys Trp Thr Val Tyr His Gly Ala Gly Thr Arg
            1075                1080                1085
Thr Ile Ala Ser Pro Lys Gly Pro Val Ile Gln Met Tyr Thr Asn Val
        1090                1095                1100
```

```
Asp Gln Asp Leu Val Gly Trp Pro Ala Pro Gln Gly Ser Arg Ser Leu
1105                1110                1115                1120

Thr Pro Cys Thr Cys Gly Ser Ser Asp Leu Tyr Leu Val Thr Arg His
            1125                1130                1135

Ala Asp Val Ile Pro Val Arg Arg Gly Asp Ser Arg Gly Ser Leu
        1140                1145                1150

Leu Ser Pro Arg Pro Ile Ser Tyr Leu Lys Gly Ser Ser Gly Gly Pro
            1155                1160                1165

Leu Leu Cys Pro Ala Gly His Ala Val Gly Leu Phe Arg Ala Ala Val
        1170                1175                1180

Cys Thr Arg Gly Val Ala Lys Ala Val Asp Phe Ile Pro Val Glu Asn
1185                1190                1195                1200

Leu Glu Thr Thr Met Arg Ser Pro Val Phe Thr Asp Asn Ser Ser Pro
                1205                1210                1215

Pro Ala Val Pro Gln Ser Phe Gln Val Ala His Leu His Ala Pro Thr
            1220                1225                1230

Gly Ser Gly Lys Ser Thr Lys Val Pro Ala Ala Tyr Ala Ala Gln Gly
            1235                1240                1245

Tyr Lys Val Leu Val Leu Asn Pro Ser Val Ala Ala Thr Leu Gly Phe
        1250                1255                1260

Gly Ala Tyr Met Ser Lys Ala His Gly Val Asp Pro Asn Ile Arg Thr
1265                1270                1275                1280

Gly Val Arg Thr Ile Thr Thr Gly Ser Pro Ile Thr Tyr Ser Thr Tyr
                1285                1290                1295

Gly Lys Phe Leu Ala Asp Gly Gly Cys Ser Gly Gly Ala Tyr Asp Ile
                1300                1305                1310

Ile Ile Cys Asp Glu Cys His Ser Thr Asp Ala Thr Ser Ile Leu Gly
            1315                1320                1325

Ile Gly Thr Val Leu Asp Gln Ala Glu Thr Ala Gly Ala Arg Leu Val
            1330                1335                1340

Val Leu Ala Thr Ala Thr Pro Pro Gly Ser Val Thr Val Ser His Pro
1345                1350                1355                1360

Asn Ile Glu Glu Val Ala Leu Ser Thr Thr Gly Glu Ile Pro Phe Tyr
                1365                1370                1375

Gly Lys Ala Ile Pro Leu Glu Val Ile Lys Gly Gly Arg His Leu Ile
            1380                1385                1390

Phe Cys His Ser Lys Lys Lys Cys Asp Glu Leu Ala Ala Lys Leu Val
            1395                1400                1405

Ala Leu Gly Ile Asn Ala Val Ala Tyr Tyr Arg Gly Leu Asp Val Ser
        1410                1415                1420

Val Ile Pro Thr Ser Gly Asp Val Val Val Val Ser Thr Asp Ala Leu
1425                1430                1435                1440

Met Thr Gly Phe Thr Gly Asp Phe Asp Ser Val Ile Asp Cys Asn Thr
                1445                1450                1455

Cys Val Thr Gln Thr Val Asp Phe Ser Leu Asp Pro Thr Phe Thr Ile
            1460                1465                1470

Glu Thr Thr Thr Leu Pro Gln Asp Ala Val Ser Arg Thr Gln Arg Arg
            1475                1480                1485

Gly Arg Thr Gly Arg Gly Lys Pro Gly Ile Tyr Arg Phe Val Ala Pro
        1490                1495                1500

Gly Glu Arg Pro Ser Gly Met Phe Asp Ser Ser Val Leu Cys Glu Cys
1505                1510                1515                1520
```

```
Tyr Asp Ala Gly Cys Ala Trp Tyr Glu Leu Thr Pro Ala Glu Thr Thr
            1525                1530                1535

Val Arg Leu Arg Ala Tyr Met Asn Thr Pro Gly Leu Pro Val Cys Gln
            1540                1545                1550

Asp His Leu Glu Phe Trp Glu Gly Val Phe Thr Gly Leu Thr His Ile
            1555                1560                1565

Asp Ala His Phe Leu Ser Gln Thr Lys Gln Ser Gly Glu Asn Phe Pro
            1570                1575                1580

Tyr Leu Val Ala Tyr Gln Ala Thr Val Cys Ala Arg Ala Gln Ala Pro
1585                1590                1595                1600

Pro Pro Ser Trp Asp Gln Met Trp Lys Cys Leu Ile Arg Leu Lys Pro
                1605                1610                1615

Thr Leu His Gly Pro Thr Pro Leu Leu Tyr Arg Leu Gly Ala Val Gln
            1620                1625                1630

Asn Glu Val Thr Leu Thr His Pro Ile Thr Lys Tyr Ile Met Thr Cys
            1635                1640                1645

Met Ser Ala Asp Leu Glu Val Val Thr Ser Thr Trp Val Leu Val Gly
            1650                1655                1660

Gly Val Leu Ala Ala Leu Ala Ala Tyr Cys Leu Ser Thr Gly Cys Val
1665                1670                1675                1680

Val Ile Val Gly Arg Ile Val Leu Ser Gly Lys Pro Ala Ile Ile Pro
            1685                1690                1695

Asp Arg Glu Val Leu Tyr Gln Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
            1730                1735                1740

Val Ile Thr Pro Ala Val Gln Thr Asn Trp Gln Lys Leu Glu Val Phe
1745                1750                1755                1760

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Gly Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Ile Gly
1825                1830                1835                1840

Ser Val Gly Leu Gly Lys Val Leu Val Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                1920

Ala Phe Ala Ser Arg Gly Asn His Val Ser Pro Thr His Tyr Val Pro
            1925                1930                1935

Glu Ser Asp Ala Ala Ala Arg Val Thr Ala Ile Leu Ser Ser Leu Thr
```

-continued

```
            1940                1945                1950
Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                2000

Pro Gln Leu Pro Gly Ile Pro Phe Val Ser Cys Gln Arg Gly Tyr Arg
                2005                2010                2015

Gly Val Trp Arg Gly Asp Gly Ile Met His Thr Arg Cys His Cys Gly
            2020                2025                2030

Ala Glu Ile Thr Gly His Val Lys Asn Gly Thr Met Arg Ile Val Gly
            2035                2040                2045

Pro Arg Thr Cys Arg Asn Met Trp Ser Gly Thr Phe Pro Ile Asn Ala
            2050                2055                2060

Tyr Thr Thr Gly Pro Cys Thr Pro Leu Pro Ala Pro Asn Tyr Lys Phe
2065                2070                2075                2080

Ala Leu Trp Arg Val Ser Ala Glu Glu Tyr Val Glu Ile Arg Arg Val
            2085                2090                2095

Gly Asp Phe His Tyr Val Ser Gly Met Thr Thr Asp Asn Leu Lys Cys
            2100                2105                2110

Pro Cys Gln Ile Pro Ser Pro Glu Phe Phe Thr Glu Leu Asp Gly Val
            2115                2120                2125

Arg Leu His Arg Phe Ala Pro Pro Cys Lys Pro Leu Leu Arg Glu Glu
            2130                2135                2140

Val Ser Phe Arg Val Gly Leu His Glu Tyr Pro Val Gly Ser Gln Leu
2145                2150                2155                2160

Pro Cys Glu Pro Glu Pro Asp Val Ala Val Leu Thr Ser Met Leu Thr
            2165                2170                2175

Asp Pro Ser His Ile Thr Ala Glu Ala Ala Gly Arg Arg Leu Ala Arg
            2180                2185                2190

Gly Ser Pro Pro Ser Met Ala Ser Ser Ser Ala Ser Gln Leu Ser Ala
            2195                2200                2205

Pro Ser Leu Lys Ala Thr Cys Thr Ala Asn His Asp Ser Pro Asp Ala
            2210                2215                2220

Glu Leu Ile Glu Ala Asn Leu Leu Trp Arg Gln Glu Met Gly Gly Asn
2225                2230                2235                2240

Ile Thr Arg Val Glu Ser Glu Asn Lys Val Val Ile Leu Asp Ser Phe
            2245                2250                2255

Asp Pro Leu Val Ala Glu Glu Asp Glu Arg Glu Val Ser Val Pro Ala
            2260                2265                2270

Glu Ile Leu Arg Lys Ser Arg Arg Phe Ala Arg Ala Leu Pro Val Trp
            2275                2280                2285

Ala Arg Pro Asp Tyr Asn Pro Pro Leu Val Glu Thr Trp Lys Lys Pro
            2290                2295                2300

Asp Tyr Glu Pro Pro Val Val His Gly Cys Pro Leu Pro Pro Pro Arg
2305                2310                2315                2320

Ser Pro Pro Val Pro Pro Pro Arg Lys Lys Arg Thr Val Val Leu Thr
                2325                2330                2335

Glu Ser Thr Leu Ser Thr Ala Leu Ala Glu Leu Ala Thr Lys Ser Phe
            2340                2345                2350

Gly Ser Ser Ser Thr Ser Gly Ile Thr Gly Asp Asn Thr Thr Thr Ser
            2355                2360                2365
```

-continued

```
Ser Glu Pro Ala Pro Ser Gly Cys Pro Pro Asp Ser Asp Val Glu Ser
    2370            2375                2380
Tyr Ser Ser Met Pro Pro Leu Glu Gly Glu Pro Gly Asp Pro Asp Leu
2385            2390                2395                2400
Ser Asp Gly Ser Trp Ser Thr Val Ser Ser Gly Ala Asp Thr Glu Asp
            2405                2410                2415
Val Val Cys Cys Ser Met Ser Tyr Ser Trp Thr Gly Ala Leu Val Thr
            2420                2425                2430
Pro Cys Ala Ala Glu Glu Gln Lys Leu Pro Ile Asn Ala Leu Ser Asn
        2435                2440                2445
Ser Leu Leu Arg His His Asn Leu Val Tyr Ser Thr Thr Ser Arg Ser
    2450                2455                2460
Ala Cys Gln Arg Gln Lys Lys Val Thr Phe Asp Arg Leu Gln Val Leu
2465                2470                2475                2480
Asp Ser His Tyr Gln Asp Val Leu Lys Glu Val Lys Ala Ala Ala Ser
            2485                2490                2495
Lys Val Lys Ala Asn Leu Leu Ser Val Glu Glu Ala Cys Ser Leu Thr
            2500                2505                2510
Pro Pro His Ser Ala Lys Ser Lys Phe Gly Tyr Gly Ala Lys Asp Val
        2515                2520                2525
Arg Cys His Ala Arg Lys Ala Val Ala His Ile Asn Ser Val Trp Lys
    2530                2535                2540
Asp Leu Leu Glu Asp Ser Val Thr Pro Ile Asp Thr Thr Ile Met Ala
2545                2550                2555                2560
Lys Asn Glu Val Phe Cys Val Gln Pro Glu Lys Gly Gly Arg Lys Pro
            2565                2570                2575
Ala Arg Leu Ile Val Phe Pro Asp Leu Gly Val Arg Val Cys Glu Lys
            2580                2585                2590
Met Ala Leu Tyr Asp Val Val Ser Lys Leu Pro Leu Ala Val Met Gly
        2595                2600                2605
Ser Ser Tyr Gly Phe Gln Tyr Ser Pro Gly Gln Arg Val Glu Phe Leu
    2610                2615                2620
Val Gln Ala Trp Lys Ser Lys Lys Thr Pro Met Gly Phe Ser Tyr Asp
2625                2630                2635                2640
Thr Arg Cys Phe Asp Ser Thr Val Thr Glu Ser Asp Ile Arg Thr Glu
            2645                2650                2655
Glu Ala Ile Tyr Gln Cys Cys Asp Leu Asp Pro Gln Ala Arg Val Ala
            2660                2665                2670
Ile Lys Ser Leu Thr Glu Arg Leu Tyr Val Gly Gly Pro Leu Thr Asn
        2675                2680                2685
Ser Arg Gly Glu Asn Cys Gly Tyr Arg Arg Cys Arg Ala Ser Gly Val
    2690                2695                2700
Leu Thr Thr Ser Cys Gly Asn Thr Leu Thr Cys Tyr Ile Lys Ala Arg
2705                2710                2715                2720
Ala Ala Cys Arg Ala Ala Gly Leu Gln Asp Cys Thr Met Leu Val Cys
            2725                2730                2735
Gly Asp Asp Leu Val Val Ile Cys Glu Ser Ala Gly Val Gln Glu Asp
            2740                2745                2750
Ala Ala Ser Leu Arg Ala Phe Thr Glu Ala Met Thr Arg Tyr Ser Ala
        2755                2760                2765
Pro Pro Gly Asp Pro Pro Gln Pro Glu Tyr Asp Leu Glu Leu Ile Thr
    2770                2775                2780
```

```
Ser Cys Ser Ser Asn Val Ser Val Ala His Asp Gly Ala Gly Lys Arg
2785                2790                2795                2800

Val Tyr Tyr Leu Thr Arg Asp Pro Thr Thr Pro Leu Ala Arg Ala Ala
            2805                2810                2815

Trp Glu Thr Ala Arg His Thr Pro Val Asn Ser Trp Leu Gly Asn Ile
        2820                2825                2830

Ile Met Phe Ala Pro Thr Leu Trp Ala Arg Met Ile Leu Met Thr His
    2835                2840                2845

Phe Phe Ser Val Leu Ile Ala Arg Asp Gln Leu Glu Gln Ala Leu Asn
2850                2855                2860

Cys Glu Ile Tyr Gly Ala Cys Tyr Ser Ile Glu Pro Leu Asp Leu Pro
2865                2870                2875                2880

Pro Ile Ile Gln Arg Leu His Gly Leu Ser Ala Phe Ser Leu His Ser
            2885                2890                2895

Tyr Ser Pro Gly Glu Ile Asn Arg Val Ala Ala Cys Leu Arg Lys Leu
        2900                2905                2910

Gly Val Pro Pro Leu Arg Ala Trp Arg His Arg Ala Arg Ser Val Arg
    2915                2920                2925

Ala Arg Leu Leu Ser Arg Gly Gly Arg Ala Ala Ile Cys Gly Lys Tyr
2930                2935                2940

Leu Phe Asn Trp Ala Val Arg Thr Lys Leu Lys Leu Thr Pro Ile Ala
2945                2950                2955                2960

Ala Ala Gly Arg Leu Asp Leu Ser Gly Trp Phe Thr Ala Gly Tyr Ser
            2965                2970                2975

Gly Gly Asp Ile Tyr His Ser Val Ser His Ala Arg Pro Arg Trp Phe
        2980                2985                2990

Trp Phe Cys Leu Leu Leu Ala Ala Gly Val Gly Ile Tyr Leu Leu
    2995                3000                3005

Pro Asn Arg
    3010

<210> SEQ ID NO 34
<211> LENGTH: 397
<212> TYPE: PRT
<213> ORGANISM: Chlamydia trachomatis

<400> SEQUENCE: 34

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Val Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Gly Leu
            85                  90                  95

Gln Asn Asp Pro Thr Thr Asn Val Ala Arg Pro Asn Pro Ala Tyr Gly
        100                 105                 110

Lys His Met Gln Asp Ala Glu Met Phe Thr Asn Ala Ala Tyr Met Ala
    115                 120                 125

Leu Asn Ile Trp Asp Arg Phe Asp Val Phe Cys Thr Leu Gly Ala Thr
    130                 135                 140
```

-continued

```
Thr Gly Tyr Leu Lys Gly Asn Ser Ala Ser Phe Asn Leu Val Gly Leu
145                 150                 155                 160

Phe Gly Thr Lys Thr Gln Ser Ser Phe Asn Thr Ala Lys Leu Ile
                165                 170                 175

Pro Asn Thr Ala Leu Asn Glu Ala Val Val Glu Leu Tyr Ile Asn Thr
                180                 185                 190

Thr Phe Ala Trp Ser Val Gly Ala Arg Ala Ala Leu Trp Glu Cys Gly
                195                 200                 205

Cys Ala Thr Leu Gly Ala Ser Phe Gln Tyr Ala Gln Ser Lys Pro Lys
                210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asn Ile Thr Ala
                245                 250                 255

Gly Thr Glu Ala Ala Thr Gly Thr Lys Asp Ala Ser Ile Asp Tyr His
                260                 265                 270

Glu Trp Gln Ala Ser Leu Ala Leu Ser Tyr Arg Leu Asn Met Phe Thr
                275                 280                 285

Pro Tyr Ile Gly Val Lys Trp Ser Arg Val Ser Phe Asp Ala Asp Thr
                290                 295                 300

Ile Arg Ile Ala Gln Pro Lys Leu Ala Glu Ala Ile Leu Asp Val Thr
305                 310                 315                 320

Thr Leu Asn Pro Thr Ile Ala Gly Lys Gly Ser Val Val Ser Ala Gly
                325                 330                 335

Thr Asp Asn Glu Leu Ala Asp Thr Met Gln Ile Val Ser Leu Gln Leu
                340                 345                 350

Asn Lys Met Lys Ser Arg Lys Ser Cys Gly Ile Ala Val Gly Thr Thr
                355                 360                 365

Ile Val Asp Ala Asp Lys Tyr Ala Val Thr Val Glu Ala Arg Leu Ile
                370                 375                 380

Asp Glu Arg Ala Ala His Val Asn Ala Gln Phe Arg Phe
385                 390                 395
```